(12) United States Patent
Moberg

(10) Patent No.: US 9,119,662 B2
(45) Date of Patent: Sep. 1, 2015

(54) MATERIAL REMOVAL DEVICE AND METHOD OF USE

(75) Inventor: John Robert Moberg, Elk River, MN (US)

(73) Assignee: Covidien LP, Mansfield, MA (US)

(*) Notice: Subject to any disclaimer, the term of this patent is extended or adjusted under 35 U.S.C. 154(b) by 389 days.

(21) Appl. No.: 13/160,044

(22) Filed: Jun. 14, 2011

(65) Prior Publication Data
US 2011/0306995 A1 Dec. 15, 2011

Related U.S. Application Data

(60) Provisional application No. 61/354,487, filed on Jun. 14, 2010.

(51) Int. Cl.
*A61B 17/22* (2006.01)
*A61B 17/3207* (2006.01)

(52) U.S. Cl.
CPC ............. *A61B 17/320783* (2013.01); *A61B 2017/320791* (2013.01)

(58) Field of Classification Search
CPC ............. A61B 17/320758; A61B 17/320725; A61B 17/321783; A61B 17/3207; A61B 2017/320004; A61B 2017/320791
USPC .......................................................... 606/159
See application file for complete search history.

(56) References Cited

U.S. PATENT DOCUMENTS

| | | | |
|---|---|---|---|
| 1,481,078 A | 1/1924 | Albertson |
| 2,178,790 A | 11/1939 | Henry |
| 2,701,559 A | 2/1955 | Cooper |
| 2,850,007 A | 9/1958 | Lingley |
| 3,064,651 A | 11/1960 | Henderson |
| 3,082,805 A | 3/1963 | Royce |
| 3,320,957 A | 5/1967 | Sokolik |

(Continued)

FOREIGN PATENT DOCUMENTS

| | | |
|---|---|---|
| CA | 2000621 | 4/1990 |
| DE | 3732236 C1 | 12/1988 |

(Continued)

OTHER PUBLICATIONS

Brezinski et al., "Optical Coherence Tomography for Optical Biopsy," Circulation, 93:1206-1213 (1996).

(Continued)

*Primary Examiner* — Thomas McEvoy
*Assistant Examiner* — Julie A Szpira

(57) ABSTRACT

A catheter having a tubular body and a rotatable shaft disposed within a lumen of the tubular body. A cutting element is coupled to the rotatable shaft, the cutting element having a cutting edge, the cutting element and rotatable shaft being longitudinally moveable within the tubular body between a stored position in which the cutting element is positioned distal of a side opening and a cutting position in which the cutting element is contained within the lumen of the tubular body and longitudinally aligned with the side opening. The cutting element is configured to extend through the side opening and to cut material from the wall of a vessel at a treatment site as the catheter is pulled proximally through the treatment site. The catheter may optionally have a rotating distal tip with an abrasive surface. The catheter includes a collection chamber positioned proximally of the cutting window.

41 Claims, 18 Drawing Sheets

(56) References Cited

U.S. PATENT DOCUMENTS

| | | |
|---|---|---|
| 3,614,953 A | 10/1971 | Moss |
| 3,683,891 A | 8/1972 | Eskridge et al. |
| 3,705,577 A | 12/1972 | Sierra |
| 3,732,858 A | 5/1973 | Banko |
| 3,749,085 A | 7/1973 | Wilson et al. |
| 3,800,783 A | 4/1974 | Jamshidi |
| 3,815,604 A | 6/1974 | O'Malley et al. |
| 3,831,585 A | 8/1974 | Brondy et al. |
| 3,837,345 A | 9/1974 | Matar |
| 3,845,375 A | 10/1974 | Stiebel |
| 3,937,222 A | 2/1976 | Banko |
| 3,945,375 A | 3/1976 | Banko |
| 3,976,077 A | 8/1976 | Kerfoot, Jr. |
| 3,995,619 A | 12/1976 | Glatzer |
| 4,007,732 A | 2/1977 | Kvavle et al. |
| 4,020,847 A | 5/1977 | Clark, III |
| 4,030,503 A | 6/1977 | Clark, III |
| 4,034,744 A | 7/1977 | Goldberg |
| 4,038,985 A | 8/1977 | Chiulli |
| 4,112,708 A | 9/1978 | Fukuda |
| 4,177,797 A | 12/1979 | Baylis et al. |
| 4,210,146 A | 7/1980 | Banko |
| 4,273,128 A | 6/1981 | Lary |
| 4,306,562 A | 12/1981 | Osborne |
| 4,306,570 A | 12/1981 | Matthews |
| 4,349,032 A | 9/1982 | Koyata |
| 4,368,730 A | 1/1983 | Sharrock |
| 4,424,045 A | 1/1984 | Kulischenko et al. |
| 4,436,091 A | 3/1984 | Banko |
| 4,445,509 A | 5/1984 | Auth |
| 4,490,139 A | 12/1984 | Huizenga et al. |
| 4,494,057 A | 1/1985 | Hotta |
| 4,512,344 A | 4/1985 | Barber |
| 4,589,412 A | 5/1986 | Kensey |
| 4,603,694 A | 8/1986 | Wheeler |
| 4,620,547 A | 11/1986 | Boebel |
| 4,631,052 A | 12/1986 | Kensey |
| 4,646,719 A | 3/1987 | Neuman et al. |
| 4,646,736 A | 3/1987 | Auth |
| 4,646,738 A | 3/1987 | Trott |
| 4,649,919 A | 3/1987 | Thimsen et al. |
| 4,653,496 A | 3/1987 | Bundy et al. |
| 4,664,112 A | 5/1987 | Kensey et al. |
| 4,669,469 A | 6/1987 | Gifford, III et al. |
| 4,679,558 A | 7/1987 | Kensey et al. |
| 4,686,982 A | 8/1987 | Nash |
| 4,692,141 A | 9/1987 | Mahurkar |
| 4,696,298 A | 9/1987 | Higgins et al. |
| 4,696,667 A | 9/1987 | Masch |
| 4,705,038 A | 11/1987 | Sjostrom |
| 4,706,671 A | 11/1987 | Weinrib |
| 4,728,319 A | 3/1988 | Masch |
| 4,729,763 A | 3/1988 | Henrie |
| 4,730,616 A | 3/1988 | Frisbie et al. |
| 4,732,154 A | 3/1988 | Shiber |
| 4,733,662 A | 3/1988 | DeSatnick et al. |
| 4,745,919 A | 5/1988 | Bundey et al. |
| 4,747,406 A | 5/1988 | Nash |
| 4,747,821 A | 5/1988 | Kensey et al. |
| 4,749,376 A | 6/1988 | Kensey et al. |
| 4,754,755 A | 7/1988 | Husted |
| 4,757,819 A | 7/1988 | Yokoi et al. |
| 4,765,332 A | 8/1988 | Fischell et al. |
| 4,771,774 A | 9/1988 | Simpson et al. |
| 4,781,186 A | 11/1988 | Simpson et al. |
| 4,784,636 A | 11/1988 | Rydell |
| 4,790,812 A | 12/1988 | Hawkins, Jr. et al. |
| 4,794,931 A | 1/1989 | Yock |
| 4,817,613 A | 4/1989 | Jaraczewski et al. |
| 4,819,634 A | 4/1989 | Shiber |
| 4,819,635 A | 4/1989 | Shapiro |
| 4,838,268 A | 6/1989 | Keith et al. |
| 4,842,579 A | 6/1989 | Shiber |
| 4,844,064 A | 7/1989 | Thimsen et al. |
| 4,848,343 A | 7/1989 | Wallsten et al. |
| 4,850,957 A | 7/1989 | Summers |
| 4,857,046 A | 8/1989 | Stevens et al. |
| 4,867,157 A | 9/1989 | McGurk-Burleson et al. |
| 4,870,953 A | 10/1989 | DonMicheal et al. |
| 4,883,458 A | 11/1989 | Shiber |
| 4,886,061 A | 12/1989 | Fischell et al. |
| 4,886,490 A | 12/1989 | Shiber |
| 4,887,613 A | 12/1989 | Farr et al. |
| 4,894,051 A | 1/1990 | Shiber |
| 4,899,757 A | 2/1990 | Pope, Jr. et al. |
| 4,919,133 A | 4/1990 | Chiang |
| 4,923,462 A | 5/1990 | Stevens |
| 4,926,858 A | 5/1990 | Gifford, III et al. |
| 4,928,693 A | 5/1990 | Goodin et al. |
| 4,936,987 A | 6/1990 | Persinski et al. |
| RE33,258 E | 7/1990 | Onik et al. |
| 4,950,238 A | 8/1990 | Sullivan |
| 4,954,338 A | 9/1990 | Mattox |
| 4,957,482 A | 9/1990 | Shiber |
| 4,966,604 A | 10/1990 | Reiss |
| 4,973,409 A | 11/1990 | Cook |
| 4,979,939 A | 12/1990 | Shiber |
| 4,979,951 A | 12/1990 | Simpson |
| 4,986,807 A | 1/1991 | Farr |
| 4,990,134 A | 2/1991 | Auth |
| 4,994,067 A | 2/1991 | Summers |
| 4,997,435 A | 3/1991 | Demeter |
| 5,000,185 A | 3/1991 | Yock |
| 5,002,553 A | 3/1991 | Shiber |
| 5,003,918 A | 4/1991 | Olson et al. |
| 5,007,896 A | 4/1991 | Shiber |
| 5,009,659 A | 4/1991 | Hamlin et al. |
| 5,019,088 A | 5/1991 | Farr |
| 5,024,234 A | 6/1991 | Leary et al. |
| 5,024,651 A | 6/1991 | Shiber |
| 5,026,384 A | 6/1991 | Farr et al. |
| 5,029,588 A | 7/1991 | Yock et al. |
| 5,030,201 A | 7/1991 | Palestrant |
| 5,047,040 A | 9/1991 | Simpson et al. |
| 5,049,124 A | 9/1991 | Bales, Jr. |
| 5,053,044 A | 10/1991 | Mueller et al. |
| 5,054,492 A | 10/1991 | Scribner et al. |
| 5,064,435 A | 11/1991 | Porter |
| 5,071,425 A | 12/1991 | Gifford et al. |
| 5,074,841 A | 12/1991 | Ademovic et al. |
| 5,077,506 A | 12/1991 | Krause et al. |
| 5,078,722 A | 1/1992 | Stevens |
| 5,078,723 A | 1/1992 | Dance et al. |
| 5,084,010 A | 1/1992 | Plaia et al. |
| 5,085,662 A | 2/1992 | Willard |
| 5,087,265 A | 2/1992 | Summers |
| 5,092,839 A | 3/1992 | Kipperman |
| 5,092,873 A | 3/1992 | Simpson et al. |
| 5,095,911 A | 3/1992 | Pomeranz |
| 5,100,423 A | 3/1992 | Fearnot |
| 5,100,424 A | 3/1992 | Jang et al. |
| 5,100,426 A | 3/1992 | Nixon |
| 5,110,822 A | 5/1992 | Sherba et al. |
| 5,112,345 A | 5/1992 | Farr |
| 5,114,399 A | 5/1992 | Kovalcheck |
| 5,115,814 A | 5/1992 | Griffith et al. |
| 5,120,323 A | 6/1992 | Shockey et al. |
| 5,127,902 A | 7/1992 | Fischell |
| 5,127,917 A | 7/1992 | Niederhauser et al. |
| 5,135,531 A | 8/1992 | Shiber |
| 5,154,705 A | 10/1992 | Fleischhacker et al. |
| 5,154,724 A | 10/1992 | Andrews |
| 5,165,421 A | 11/1992 | Fleischhacker et al. |
| 5,176,693 A | 1/1993 | Pannek, Jr. |
| 5,178,625 A | 1/1993 | Groshong |
| 5,181,920 A | 1/1993 | Mueller et al. |
| 5,183,432 A | 2/1993 | Noguchi |
| 5,190,528 A | 3/1993 | Fonger et al. |
| 5,192,291 A | 3/1993 | Pannek, Jr. |
| 5,195,956 A | 3/1993 | Stockmeier |
| 5,211,651 A | 5/1993 | Reger et al. |
| 5,217,474 A | 6/1993 | Zacca et al. |
| 5,222,966 A | 6/1993 | Perkins et al. |
| 5,224,488 A | 7/1993 | Neuffer |

(56) References Cited

U.S. PATENT DOCUMENTS

| | | |
|---|---|---|
| 5,224,945 A | 7/1993 | Pannek, Jr. |
| 5,224,949 A | 7/1993 | Gomringer et al. |
| 5,226,909 A | 7/1993 | Evans et al. |
| 5,226,910 A | 7/1993 | Kajiyama et al. |
| 5,234,451 A | 8/1993 | Osypka |
| 5,242,460 A | 9/1993 | Klein et al. |
| 5,242,461 A | 9/1993 | Kortenbach et al. |
| 5,250,059 A | 10/1993 | Andreas et al. |
| 5,250,065 A | 10/1993 | Clement et al. |
| 5,263,928 A | 11/1993 | Trauthen et al. |
| 5,263,959 A | 11/1993 | Fischell |
| 5,267,955 A | 12/1993 | Hanson |
| 5,267,982 A | 12/1993 | Sylvanowicz |
| 5,269,793 A | 12/1993 | Simpson et al. |
| 5,273,526 A | 12/1993 | Dance et al. |
| 5,282,484 A | 2/1994 | Reger |
| 5,284,486 A | 2/1994 | Kotula et al. |
| 5,285,795 A | 2/1994 | Ryan et al. |
| 5,295,493 A | 3/1994 | Radisch, Jr. |
| 5,300,085 A | 4/1994 | Yock |
| 5,306,294 A | 4/1994 | Winston et al. |
| 5,308,354 A | 5/1994 | Zacca et al. |
| 5,312,425 A | 5/1994 | Evans et al. |
| 5,312,427 A | 5/1994 | Shturman |
| 5,314,438 A | 5/1994 | Shturman |
| 5,318,032 A | 6/1994 | Lonsbury et al. |
| 5,318,528 A | 6/1994 | Heaven et al. |
| 5,318,576 A | 6/1994 | Plassche, Jr. et al. |
| 5,321,501 A | 6/1994 | Swanson et al. |
| 5,322,508 A | 6/1994 | Viera |
| 5,350,390 A | 9/1994 | Sher |
| 5,356,418 A | 10/1994 | Shturman |
| 5,358,472 A | 10/1994 | Vance et al. |
| 5,358,485 A | 10/1994 | Vance et al. |
| 5,360,432 A | 11/1994 | Shturman |
| 5,364,395 A * | 11/1994 | West, Jr. .................. 606/46 |
| 5,366,463 A | 11/1994 | Ryan |
| 5,368,035 A | 11/1994 | Hamm et al. |
| 5,370,609 A | 12/1994 | Drasler et al. |
| 5,370,651 A | 12/1994 | Summers |
| 5,372,601 A | 12/1994 | Lary |
| 5,372,602 A | 12/1994 | Burke |
| 5,373,619 A | 12/1994 | Fleischhacker et al. |
| 5,373,849 A | 12/1994 | Maroney et al. |
| 5,377,682 A | 1/1995 | Ueno et al. |
| 5,378,234 A | 1/1995 | Hammerslag et al. |
| 5,383,460 A | 1/1995 | Jang et al. |
| 5,395,311 A | 3/1995 | Andrews |
| 5,395,313 A | 3/1995 | Naves et al. |
| 5,395,335 A | 3/1995 | Jang |
| 5,397,345 A | 3/1995 | Lazarus |
| 5,402,790 A | 4/1995 | Jang et al. |
| 5,403,334 A | 4/1995 | Evans et al. |
| 5,409,454 A | 4/1995 | Fischell et al. |
| 5,413,107 A | 5/1995 | Oakley et al. |
| 5,419,774 A | 5/1995 | Willard et al. |
| 5,423,740 A | 6/1995 | Sullivan |
| 5,423,799 A | 6/1995 | Shiu |
| 5,423,838 A | 6/1995 | Willard |
| 5,423,846 A | 6/1995 | Fischell |
| 5,427,107 A | 6/1995 | Milo et al. |
| 5,429,136 A | 7/1995 | Milo et al. |
| 5,431,673 A | 7/1995 | Summers et al. |
| 5,441,510 A | 8/1995 | Simpson et al. |
| 5,443,446 A | 8/1995 | Shturman |
| 5,443,497 A | 8/1995 | Venbrux |
| 5,444,078 A | 8/1995 | Yu et al. |
| 5,445,155 A | 8/1995 | Sieben |
| 5,449,369 A | 9/1995 | Imran |
| 5,451,233 A | 9/1995 | Yock |
| 5,454,809 A | 10/1995 | Janssen |
| 5,456,667 A | 10/1995 | Ham et al. |
| 5,456,689 A | 10/1995 | Kresch et al. |
| 5,458,585 A | 10/1995 | Salmon et al. |
| 5,459,570 A | 10/1995 | Swanson et al. |
| 5,464,016 A | 11/1995 | Nicholas et al. |
| 5,470,415 A | 11/1995 | Perkins et al. |
| 5,485,042 A | 1/1996 | Burke et al. |
| 5,485,840 A | 1/1996 | Bauman |
| 5,487,729 A | 1/1996 | Avellanet et al. |
| 5,489,295 A | 2/1996 | Piplani et al. |
| 5,491,524 A | 2/1996 | Hellmuth et al. |
| 5,496,267 A | 3/1996 | Drasler et al. |
| 5,501,694 A | 3/1996 | Ressemann et al. |
| 5,503,155 A | 4/1996 | Salmon et al. |
| 5,505,210 A | 4/1996 | Clement |
| 5,507,292 A | 4/1996 | Jang et al. |
| 5,507,760 A | 4/1996 | Wynne et al. |
| 5,507,761 A | 4/1996 | Duer |
| 5,507,795 A | 4/1996 | Chiang et al. |
| 5,512,044 A | 4/1996 | Duer |
| 5,514,115 A | 5/1996 | Frantzen et al. |
| 5,520,189 A | 5/1996 | Malinowski et al. |
| 5,522,825 A | 6/1996 | Kropf et al. |
| 5,522,880 A | 6/1996 | Barone et al. |
| 5,527,292 A | 6/1996 | Adams et al. |
| 5,527,298 A | 6/1996 | Vance et al. |
| 5,527,325 A | 6/1996 | Conley et al. |
| 5,531,685 A | 7/1996 | Hemmer et al. |
| 5,531,690 A | 7/1996 | Solar |
| 5,531,700 A | 7/1996 | Moore et al. |
| 5,540,707 A | 7/1996 | Ressemann et al. |
| 5,549,601 A | 8/1996 | McIntyre et al. |
| 5,554,163 A | 9/1996 | Shturman |
| 5,556,408 A | 9/1996 | Farhat |
| 5,558,093 A | 9/1996 | Pomeranz |
| 5,562,726 A | 10/1996 | Chuter |
| 5,562,728 A | 10/1996 | Lazarus et al. |
| 5,569,275 A | 10/1996 | Kotula et al. |
| 5,569,276 A | 10/1996 | Jang et al. |
| 5,569,277 A | 10/1996 | Evans et al. |
| 5,569,279 A | 10/1996 | Rainin |
| 5,570,693 A | 11/1996 | Jang et al. |
| 5,571,122 A | 11/1996 | Kelly et al. |
| 5,571,130 A | 11/1996 | Simpson et al. |
| 5,575,817 A | 11/1996 | Martin |
| 5,584,842 A | 12/1996 | Fogarty et al. |
| 5,584,843 A | 12/1996 | Wulfman et al. |
| 5,609,605 A | 3/1997 | Marshall et al. |
| 5,618,293 A | 4/1997 | Sample et al. |
| 5,620,447 A | 4/1997 | Smith et al. |
| 5,624,457 A | 4/1997 | Farley et al. |
| 5,626,562 A | 5/1997 | Castro |
| 5,626,576 A | 5/1997 | Janssen |
| 5,628,761 A | 5/1997 | Rizik |
| 5,632,754 A | 5/1997 | Farley et al. |
| 5,632,755 A | 5/1997 | Nordgren et al. |
| 5,634,464 A | 6/1997 | Jang et al. |
| 5,643,296 A | 7/1997 | Hundertmark et al. |
| 5,643,298 A | 7/1997 | Nordgren et al. |
| 5,649,941 A | 7/1997 | Lary |
| 5,660,180 A | 8/1997 | Malinowski et al. |
| 5,662,671 A | 9/1997 | Barbut et al. |
| 5,665,098 A | 9/1997 | Kelly et al. |
| 5,669,920 A | 9/1997 | Conley et al. |
| 5,674,232 A | 10/1997 | Halliburton |
| 5,676,696 A | 10/1997 | Marcade |
| 5,676,697 A | 10/1997 | McDonald |
| 5,681,336 A | 10/1997 | Clement et al. |
| 5,682,897 A | 11/1997 | Pomeranz |
| 5,683,449 A | 11/1997 | Marcade |
| 5,683,453 A | 11/1997 | Palmaz |
| 5,688,234 A | 11/1997 | Frisbie |
| 5,695,506 A | 12/1997 | Pike |
| 5,695,507 A | 12/1997 | Auth et al. |
| 5,697,944 A | 12/1997 | Lary |
| 5,700,240 A | 12/1997 | Barwick, Jr. et al. |
| 5,700,687 A | 12/1997 | Finn |
| 5,707,350 A | 1/1998 | Krause et al. |
| 5,707,376 A | 1/1998 | Kavteladze et al. |
| 5,707,383 A | 1/1998 | Bays et al. |
| 5,709,698 A | 1/1998 | Adams et al. |
| 5,713,913 A | 2/1998 | Lary et al. |
| 5,715,825 A | 2/1998 | Crowley |

(56) References Cited

U.S. PATENT DOCUMENTS

| | | |
|---|---|---|
| 5,716,410 A | 2/1998 | Wang et al. |
| 5,720,735 A | 2/1998 | Dorros |
| 5,724,977 A | 3/1998 | Yock et al. |
| 5,728,123 A | 3/1998 | Lemelson et al. |
| 5,733,296 A | 3/1998 | Rogers et al. |
| 5,735,816 A | 4/1998 | Lieber et al. |
| 5,741,270 A | 4/1998 | Hansen et al. |
| 5,766,192 A | 6/1998 | Zacca |
| 5,772,674 A | 6/1998 | Nakhjavan |
| 5,775,327 A | 7/1998 | Randolph et al. |
| 5,776,114 A | 7/1998 | Frantzen et al. |
| 5,776,153 A | 7/1998 | Rees |
| 5,779,643 A | 7/1998 | Lum et al. |
| 5,779,673 A | 7/1998 | Roth et al. |
| 5,779,721 A | 7/1998 | Nash |
| 5,779,722 A | 7/1998 | Shturman et al. |
| 5,792,157 A | 8/1998 | Mische et al. |
| 5,797,949 A | 8/1998 | Parodi |
| 5,799,655 A | 9/1998 | Jang et al. |
| 5,807,329 A | 9/1998 | Gelman |
| 5,810,867 A | 9/1998 | Zarbatany et al. |
| 5,816,923 A | 10/1998 | Milo et al. |
| 5,820,592 A | 10/1998 | Hammerslag |
| 5,823,971 A | 10/1998 | Robinson et al. |
| 5,824,039 A | 10/1998 | Piplani et al. |
| 5,824,055 A | 10/1998 | Spiridigliozzi et al. |
| 5,827,201 A | 10/1998 | Samson et al. |
| 5,827,229 A | 10/1998 | Auth et al. |
| 5,827,304 A | 10/1998 | Hart |
| 5,827,322 A | 10/1998 | Williams |
| 5,830,224 A | 11/1998 | Cohn et al. |
| 5,836,957 A | 11/1998 | Schulz et al. |
| 5,843,022 A | 12/1998 | Willard et al. |
| 5,843,103 A | 12/1998 | Wulfman |
| 5,843,161 A | 12/1998 | Solovay |
| 5,855,563 A | 1/1999 | Kaplan et al. |
| 5,865,748 A | 2/1999 | Co et al. |
| 5,868,685 A | 2/1999 | Powell et al. |
| 5,868,767 A | 2/1999 | Farley et al. |
| 5,871,536 A | 2/1999 | Lazarus |
| 5,873,882 A | 2/1999 | Straub et al. |
| 5,876,414 A | 3/1999 | Straub |
| 5,879,397 A | 3/1999 | Kalberer et al. |
| 5,883,458 A | 3/1999 | Sumita et al. |
| 5,888,201 A | 3/1999 | Stinson et al. |
| 5,895,399 A | 4/1999 | Barbut et al. |
| 5,895,402 A | 4/1999 | Hundertmark et al. |
| 5,902,245 A | 5/1999 | Yock |
| 5,910,150 A | 6/1999 | Saadat |
| 5,911,734 A | 6/1999 | Tsugita et al. |
| 5,916,210 A | 6/1999 | Winston |
| 5,922,003 A | 7/1999 | Anctil et al. |
| 5,935,108 A | 8/1999 | Katoh et al. |
| 5,938,645 A | 8/1999 | Gordon |
| 5,938,671 A | 8/1999 | Katoh et al. |
| 5,938,672 A | 8/1999 | Nash |
| 5,941,869 A | 8/1999 | Patterson et al. |
| 5,947,985 A | 9/1999 | Imran |
| 5,948,184 A | 9/1999 | Frantzen et al. |
| 5,951,480 A | 9/1999 | White et al. |
| 5,951,482 A | 9/1999 | Winston et al. |
| 5,954,745 A | 9/1999 | Gertler et al. |
| 5,968,064 A | 10/1999 | Selmon et al. |
| 5,972,019 A | 10/1999 | Engelson et al. |
| 5,985,397 A | 11/1999 | Witt et al. |
| 5,989,281 A | 11/1999 | Barbut et al. |
| 5,997,557 A | 12/1999 | Barbut et al. |
| 6,001,112 A | 12/1999 | Taylor |
| 6,010,449 A | 1/2000 | Selmon et al. |
| 6,010,522 A | 1/2000 | Barbut et al. |
| 6,013,072 A | 1/2000 | Winston et al. |
| 6,019,778 A | 2/2000 | Wislon et al. |
| 6,022,362 A | 2/2000 | Lee et al. |
| 6,027,450 A | 2/2000 | Brown et al. |
| 6,027,460 A | 2/2000 | Shturman |
| 6,027,514 A | 2/2000 | Stine et al. |
| 6,032,673 A | 3/2000 | Savage et al. |
| 6,036,646 A | 3/2000 | Barthe et al. |
| 6,036,656 A | 3/2000 | Slater |
| 6,036,707 A | 3/2000 | Spaulding |
| 6,048,349 A | 4/2000 | Winston et al. |
| 6,050,949 A | 4/2000 | White et al. |
| 6,063,093 A | 5/2000 | Winston et al. |
| 6,066,153 A | 5/2000 | Lev |
| 6,068,603 A | 5/2000 | Suzuki |
| 6,068,638 A | 5/2000 | Makower |
| 6,081,738 A | 6/2000 | Hinohara et al. |
| RE36,764 E | 7/2000 | Zacca et al. |
| 6,095,990 A | 8/2000 | Parodi |
| 6,099,542 A | 8/2000 | Cohn et al. |
| 6,106,515 A | 8/2000 | Winston et al. |
| 6,110,121 A | 8/2000 | Lenker |
| 6,120,515 A | 9/2000 | Rogers et al. |
| 6,120,516 A | 9/2000 | Selmon et al. |
| 6,126,649 A | 10/2000 | VanTassel et al. |
| 6,129,734 A | 10/2000 | Shturman et al. |
| 6,134,003 A | 10/2000 | Tearney et al. |
| 6,152,909 A | 11/2000 | Bagaoisan et al. |
| 6,152,938 A | 11/2000 | Curry |
| 6,156,046 A | 12/2000 | Passafaro et al. |
| 6,156,047 A * | 12/2000 | Spaulding ............. 606/159 |
| 6,157,852 A | 12/2000 | Selmon et al. |
| 6,159,195 A | 12/2000 | Ha et al. |
| 6,159,225 A | 12/2000 | Makower |
| 6,165,127 A | 12/2000 | Crowley |
| 6,179,859 B1 | 1/2001 | Bates et al. |
| 6,183,432 B1 | 2/2001 | Milo |
| 6,187,025 B1 | 2/2001 | Machek |
| 6,190,353 B1 | 2/2001 | Makower et al. |
| 6,191,862 B1 | 2/2001 | Swanson et al. |
| 6,193,676 B1 | 2/2001 | Winston et al. |
| 6,196,963 B1 | 3/2001 | Williams |
| 6,206,898 B1 | 3/2001 | Honeycutt et al. |
| 6,217,527 B1 | 4/2001 | Selmon et al. |
| 6,217,549 B1 | 4/2001 | Selmon et al. |
| 6,217,595 B1 | 4/2001 | Shturman et al. |
| 6,221,049 B1 | 4/2001 | Selmon et al. |
| 6,221,332 B1 | 4/2001 | Thumm et al. |
| 6,228,049 B1 | 5/2001 | Schroeder et al. |
| 6,228,076 B1 | 5/2001 | Winston et al. |
| 6,231,546 B1 | 5/2001 | Milo et al. |
| 6,231,549 B1 | 5/2001 | Noecker et al. |
| 6,235,000 B1 | 5/2001 | Milo et al. |
| 6,238,405 B1 | 5/2001 | Findlay, III et al. |
| 6,241,667 B1 | 6/2001 | Vetter et al. |
| 6,241,744 B1 | 6/2001 | Imran et al. |
| 6,245,012 B1 | 6/2001 | Kleshinski |
| 6,258,052 B1 | 7/2001 | Milo |
| 6,263,236 B1 | 7/2001 | Kasinkas et al. |
| 6,264,611 B1 | 7/2001 | Ishikawa et al. |
| 6,266,550 B1 | 7/2001 | Selmon et al. |
| 6,277,138 B1 | 8/2001 | Levinson et al. |
| 6,283,951 B1 | 9/2001 | Flaherty et al. |
| 6,283,983 B1 | 9/2001 | Makower et al. |
| 6,299,622 B1 | 10/2001 | Snow et al. |
| 6,299,623 B1 | 10/2001 | Wulfman |
| 6,302,875 B1 | 10/2001 | Makower et al. |
| 6,305,834 B1 | 10/2001 | Schubert et al. |
| 6,312,444 B1 | 11/2001 | Barbut |
| 6,319,242 B1 | 11/2001 | Patterson et al. |
| 6,319,275 B1 | 11/2001 | Lashinski et al. |
| 6,330,884 B1 | 12/2001 | Kim |
| 6,355,005 B1 | 3/2002 | Powell et al. |
| 6,361,545 B1 | 3/2002 | Macoviak et al. |
| 6,375,615 B1 | 4/2002 | Flaherty et al. |
| 6,383,195 B1 | 5/2002 | Richard |
| 6,383,205 B1 | 5/2002 | Samson et al. |
| 6,394,976 B1 | 5/2002 | Winston et al. |
| 6,398,798 B2 | 6/2002 | Selmon et al. |
| 6,422,736 B1 | 7/2002 | Antonaides et al. |
| 6,423,081 B1 | 7/2002 | Lee et al. |
| 6,425,870 B1 | 7/2002 | Flesch |
| 6,428,551 B1 | 8/2002 | Hall et al. |
| 6,428,552 B1 | 8/2002 | Sparks |

(56) References Cited

U.S. PATENT DOCUMENTS

| | | |
|---|---|---|
| 6,443,966 B1 | 9/2002 | Shiu |
| 6,445,939 B1 | 9/2002 | Swanson et al. |
| 6,447,525 B2 | 9/2002 | Follmer et al. |
| 6,451,036 B1 | 9/2002 | Heitzmann et al. |
| 6,454,779 B1 | 9/2002 | Taylor |
| 6,475,226 B1 | 11/2002 | Belef et al. |
| 6,482,217 B1 | 11/2002 | Pintor et al. |
| 6,497,711 B1 | 12/2002 | Plaia et al. |
| 6,501,551 B1 | 12/2002 | Tearney et al. |
| 6,520,975 B2 | 2/2003 | Branco |
| RE38,018 E | 3/2003 | Anctil et al. |
| 6,532,380 B1 | 3/2003 | Close et al. |
| 6,533,749 B1 | 3/2003 | Mitusina et al. |
| 6,561,998 B1 | 5/2003 | Roth et al. |
| 6,565,588 B1 | 5/2003 | Clement et al. |
| 6,569,177 B1 | 5/2003 | Dillard et al. |
| 6,592,526 B1 | 7/2003 | Lenker |
| 6,610,059 B1 | 8/2003 | West, Jr. |
| 6,620,180 B1 | 9/2003 | Bays et al. |
| 6,623,437 B2 | 9/2003 | Hinchliffe et al. |
| 6,623,495 B2 | 9/2003 | Findlay, III et al. |
| 6,623,496 B2 | 9/2003 | Snow et al. |
| 6,629,953 B1 | 10/2003 | Boyd |
| 6,638,233 B2 | 10/2003 | Corvi et al. |
| RE38,335 E | 11/2003 | Aust et al. |
| 6,652,505 B1 | 11/2003 | Tsugita |
| 6,652,548 B2 | 11/2003 | Evans et al. |
| 6,656,195 B2 | 12/2003 | Peters et al. |
| 6,666,874 B2 | 12/2003 | Heitzmann et al. |
| 6,682,543 B2 | 1/2004 | Barbut et al. |
| 6,733,511 B2 | 5/2004 | Hall et al. |
| 6,740,103 B2 | 5/2004 | Hall et al. |
| 6,746,462 B1 | 6/2004 | Selmon et al. |
| 6,764,495 B2 | 7/2004 | Lee et al. |
| 6,790,204 B2 | 9/2004 | Zadno-Azizi et al. |
| 6,790,215 B2 | 9/2004 | Findlay, III et al. |
| 6,818,001 B2 | 11/2004 | Wulfman et al. |
| 6,830,577 B2 | 12/2004 | Nash et al. |
| 6,843,797 B2 | 1/2005 | Nash et al. |
| 6,849,068 B1 | 2/2005 | Bagaoisan et al. |
| 6,863,676 B2 | 3/2005 | Lee et al. |
| 6,911,026 B1 | 6/2005 | Hall et al. |
| 6,970,732 B2 | 11/2005 | Winston et al. |
| 6,997,934 B2 | 2/2006 | Snow et al. |
| 7,153,315 B2 | 12/2006 | Miller |
| 7,172,610 B2 | 2/2007 | Heitzmann et al. |
| 7,208,511 B2 | 4/2007 | Williams et al. |
| 7,235,088 B2 | 6/2007 | Pintor et al. |
| 7,318,831 B2 | 1/2008 | Alvarez et al. |
| 7,388,495 B2 | 6/2008 | Fallin et al. |
| 7,479,148 B2 | 1/2009 | Beaupre |
| 7,488,322 B2 | 2/2009 | Brunnett et al. |
| 7,524,289 B2 | 4/2009 | Lenker |
| 7,603,166 B2 | 10/2009 | Casscells, III et al. |
| 7,708,749 B2 * | 5/2010 | Simpson et al. ............... 606/159 |
| 7,713,235 B2 | 5/2010 | Torrance et al. |
| 7,713,279 B2 | 5/2010 | Simpson et al. |
| 7,729,745 B2 | 6/2010 | Maschke |
| 7,734,332 B2 | 6/2010 | Sher |
| 7,753,852 B2 | 7/2010 | Maschke |
| 7,758,599 B2 | 7/2010 | Snow et al. |
| 7,771,444 B2 | 8/2010 | Patel et al. |
| 7,887,556 B2 | 2/2011 | Simpson et al. |
| 8,052,704 B2 * | 11/2011 | Olson ............................ 606/159 |
| 2001/0000041 A1 | 3/2001 | Selmon et al. |
| 2001/0031784 A1 | 10/2001 | Petersen et al. |
| 2001/0031981 A1 | 10/2001 | Evans et al. |
| 2001/0044622 A1 | 11/2001 | Vardi et al. |
| 2001/0049500 A1 | 12/2001 | VanTassel et al. |
| 2002/0019644 A1 | 2/2002 | Hastings et al. |
| 2002/0022788 A1 | 2/2002 | Corvi et al. |
| 2002/0058904 A1 | 5/2002 | Boock et al. |
| 2002/0077373 A1 | 6/2002 | Hudson |
| 2002/0077642 A1 | 6/2002 | Patel et al. |
| 2002/0095141 A1 | 7/2002 | Belef et al. |
| 2002/0103459 A1 | 8/2002 | Sparks et al. |
| 2002/0177800 A1 | 11/2002 | Bagaoisan et al. |
| 2002/0188307 A1 | 12/2002 | Pintor et al. |
| 2003/0018346 A1 | 1/2003 | Follmer et al. |
| 2003/0023263 A1 | 1/2003 | Krolik et al. |
| 2003/0093098 A1 | 5/2003 | Heitzmann et al. |
| 2003/0120295 A1 | 6/2003 | Simpson et al. |
| 2003/0125757 A1 | 7/2003 | Patel et al. |
| 2003/0125758 A1 | 7/2003 | Simpson et al. |
| 2003/0163126 A1 * | 8/2003 | West, Jr. .......................... 606/41 |
| 2003/0199747 A1 | 10/2003 | Michlitsch et al. |
| 2003/0206484 A1 | 11/2003 | Childers et al. |
| 2003/0229369 A1 | 12/2003 | Findlay, III et al. |
| 2004/0006358 A1 | 1/2004 | Wulfman et al. |
| 2004/0049225 A1 | 3/2004 | Denison |
| 2004/0167553 A1 | 8/2004 | Simpson et al. |
| 2004/0167554 A1 | 8/2004 | Simpson et al. |
| 2004/0193034 A1 | 9/2004 | Wasicek et al. |
| 2004/0210245 A1 | 10/2004 | Erickson et al. |
| 2005/0004585 A1 | 1/2005 | Hall et al. |
| 2005/0004594 A1 | 1/2005 | Nool et al. |
| 2005/0021063 A1 | 1/2005 | Hall et al. |
| 2005/0042239 A1 | 2/2005 | Lipiecki et al. |
| 2005/0090845 A1 | 4/2005 | Boyd |
| 2005/0090849 A1 | 4/2005 | Adams |
| 2005/0177068 A1 | 8/2005 | Simpson |
| 2005/0216018 A1 | 9/2005 | Sennett |
| 2005/0222596 A1 | 10/2005 | Maschke |
| 2005/0222663 A1 * | 10/2005 | Simpson et al. .............. 623/1.11 |
| 2006/0015126 A1 | 1/2006 | Sher |
| 2006/0074442 A1 * | 4/2006 | Noriega et al. ................ 606/159 |
| 2006/0235334 A1 | 10/2006 | Corvi et al. |
| 2006/0259052 A1 | 11/2006 | Pintor et al. |
| 2007/0010840 A1 | 1/2007 | Rosenthal et al. |
| 2007/0038061 A1 | 2/2007 | Huennekens et al. |
| 2007/0049958 A1 | 3/2007 | Adams |
| 2007/0135712 A1 | 6/2007 | Maschke |
| 2007/0135886 A1 | 6/2007 | Maschke |
| 2007/0167824 A1 | 7/2007 | Lee et al. |
| 2007/0225739 A1 | 9/2007 | Pintor et al. |
| 2007/0265647 A1 | 11/2007 | Bonnette et al. |
| 2007/0276419 A1 | 11/2007 | Rosenthal |
| 2008/0001643 A1 | 1/2008 | Lee |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0045986 A1 | 2/2008 | To et al. |
| 2008/0051812 A1 * | 2/2008 | Schmitz et al. ............... 606/167 |
| 2008/0065124 A1 | 3/2008 | Olson |
| 2008/0065125 A1 * | 3/2008 | Olson ............................ 606/159 |
| 2008/0097403 A1 | 4/2008 | Donaldson et al. |
| 2008/0125799 A1 | 5/2008 | Adams |
| 2008/0161840 A1 | 7/2008 | Osiroff et al. |
| 2008/0177139 A1 | 7/2008 | Courtney et al. |
| 2008/0208227 A1 | 8/2008 | Kadykowski et al. |
| 2008/0249553 A1 | 10/2008 | Gruber et al. |
| 2008/0312673 A1 | 12/2008 | Viswanathan et al. |
| 2009/0012548 A1 | 1/2009 | Thatcher et al. |
| 2009/0018565 A1 | 1/2009 | To et al. |
| 2009/0018566 A1 | 1/2009 | Escudero et al. |
| 2009/0138031 A1 | 5/2009 | Tsukernik et al. |
| 2009/0187203 A1 | 7/2009 | Corvi et al. |
| 2009/0216125 A1 | 8/2009 | Lenker |
| 2009/0216180 A1 | 8/2009 | Lee et al. |
| 2009/0226063 A1 | 9/2009 | Rangwala et al. |
| 2009/0234378 A1 | 9/2009 | Escudero et al. |
| 2009/0270888 A1 | 10/2009 | Patel et al. |
| 2009/0275966 A1 | 11/2009 | Mitusina |
| 2009/0299394 A1 | 12/2009 | Simpson et al. |
| 2009/0306689 A1 | 12/2009 | Welty et al. |
| 2010/0030216 A1 | 2/2010 | Arcenio |
| 2010/0049225 A1 | 2/2010 | To et al. |
| 2010/0130996 A1 | 5/2010 | Doud et al. |
| 2010/0198240 A1 | 8/2010 | Simpson et al. |
| 2010/0241147 A1 | 9/2010 | Maschke |
| 2010/0280534 A1 | 11/2010 | Sher |
| 2010/0292721 A1 | 11/2010 | Moberg |
| 2010/0298850 A1 | 11/2010 | Snow et al. |

(56) References Cited

U.S. PATENT DOCUMENTS

| | | |
|---|---|---|
| 2010/0312263 A1 | 12/2010 | Moberg et al. |
| 2011/0004107 A1 | 1/2011 | Rosenthal et al. |
| 2011/0022069 A1 | 1/2011 | Mitusina |
| 2011/0040315 A1 | 2/2011 | To et al. |
| 2011/0130777 A1 | 6/2011 | Zhang et al. |
| 2011/0144673 A1 | 6/2011 | Zhang et al. |

FOREIGN PATENT DOCUMENTS

| | | |
|---|---|---|
| DE | 8900059 U1 | 5/1989 |
| DE | 93 03 531 U1 | 7/1994 |
| DE | 44 44 166 A1 | 6/1996 |
| DE | 29722136 U1 | 5/1999 |
| EP | 0086048 A2 | 8/1983 |
| EP | 0 107 009 A2 | 5/1984 |
| EP | 0 229 620 A2 | 7/1987 |
| EP | 0291170 A1 | 11/1988 |
| EP | 0 302 701 A2 | 2/1989 |
| EP | 0330843 A1 | 9/1989 |
| EP | 0373927 A2 | 6/1990 |
| EP | 0421457 A1 | 4/1991 |
| EP | 0 431 752 A2 | 6/1991 |
| EP | 0448859 A2 | 10/1991 |
| EP | 0463798 A1 | 1/1992 |
| EP | 0 490 565 A1 | 6/1992 |
| EP | 0514810 A1 | 11/1992 |
| EP | 0 526 042 A1 | 2/1993 |
| EP | 0533320 A2 | 3/1993 |
| EP | 0 608 911 A1 | 8/1994 |
| EP | 0 608 912 A1 | 8/1994 |
| EP | 0 611 522 A1 | 8/1994 |
| EP | 0 648 414 B1 | 4/1995 |
| EP | 0657140 A1 | 6/1995 |
| EP | 0 680 695 B1 | 11/1998 |
| EP | 0 983 749 A2 | 3/2000 |
| EP | 1 767 159 A1 | 3/2007 |
| EP | 1 875 871 A2 | 1/2008 |
| GB | 2093353 A | 9/1982 |
| GB | 2 115 829 A | 9/1983 |
| GB | 2210965 A | 6/1989 |
| JP | 2-206452 A | 8/1990 |
| JP | 2271847 A | 11/1990 |
| JP | 3186256 A | 8/1991 |
| JP | 4200459 A | 7/1992 |
| JP | 5042162 A | 2/1993 |
| JP | 5056984 A | 3/1993 |
| JP | 5184679 A | 7/1993 |
| JP | 6269460 A | 9/1994 |
| JP | 7075611 B | 8/1995 |
| JP | 2010213801 | 9/2010 |
| JP | 2012526636 | 11/2012 |
| SU | 442795 A1 | 9/1974 |
| SU | 665908 A1 | 6/1979 |
| WO | WO 8906517 A1 | 7/1989 |
| WO | WO 92/07500 A2 | 5/1992 |
| WO | WO 9313716 A1 | 7/1993 |
| WO | WO 9313717 A1 | 7/1993 |
| WO | WO 93/16642 A1 | 9/1993 |
| WO | WO 9521576 A1 | 8/1995 |
| WO | WO 9611648 A1 | 4/1996 |
| WO | WO 9746164 A1 | 12/1997 |
| WO | WO 9804199 A1 | 2/1998 |
| WO | WO 9824372 A1 | 6/1998 |
| WO | WO 99/39648 A1 | 8/1999 |
| WO | WO 9952454 A1 | 10/1999 |
| WO | WO 00/30531 A1 | 6/2000 |
| WO | WO 00/54735 A1 | 9/2000 |
| WO | WO 00/62913 A1 | 10/2000 |
| WO | WO 00/63800 A1 | 11/2000 |
| WO | WO 00/72955 A1 | 12/2000 |
| WO | WO 01/15609 A1 | 3/2001 |
| WO | WO 01/19444 A1 | 3/2001 |
| WO | WO 0130433 A1 | 5/2001 |
| WO | WO 01/43857 A1 | 6/2001 |
| WO | WO 0143809 A1 | 6/2001 |
| WO | WO 02/16017 A2 | 2/2002 |
| WO | WO 02/45598 A2 | 6/2002 |
| WO | 2006058223 A2 | 6/2006 |
| WO | 2006066012 A2 | 6/2006 |
| WO | WO 2006/058223 A2 | 6/2006 |
| WO | WO 2006/066012 A2 | 6/2006 |
| WO | 2008-042987 A2 | 4/2008 |
| WO | 2011159697 A1 | 12/2011 |

OTHER PUBLICATIONS

Brezinski et al., "Assessing Atherosclerotic Plaque Morphology: Comparison of Optical Coherence Tomography and High Frequency Intravascular Ultrasound," Heart, 77:397-403 (1997).

Huang et al., "Optical Coherence Tomography," Science, 254:1178-1181 (1991).

International Search Report and Written Opinion of PCT Application No. PCT/US04/12600, dated Jun. 13, 2008, 8 pages total.

International Search Report of PCT Application No. PCT/US04/12601, dated Jun. 30, 2005, 3 pages total.

Mar. 27, 2009 Communication from the European Patent Office regarding EP Application No. 01 991 343.3 (7 pages).

Apr. 6, 2010 European Supplementary Search Report in European Application No. 04760156.2 (3 pages).

Sep. 21, 2010 International Search Report and Written Opinion for PCT Application No. PCT/US2010/032558 (14 pages).

Abstract of JP2206452A (1 page).

Amplatz Coronary Catheters, posted: Feb. 25, 2009, [online], [retrieved on Mar. 29, 2011], retrieved from the Cardiophile MD using Internet website <URL:http://cardiophile.org/2009/02/amplatzcoronary-catheter.html> (3 pages).

Judkins Left Coronary Catheter, posted: Feb. 19, 2009, [online], [retrieved on Mar. 29, 2011], retrieved from the Cardiophile MD using Internet website <URL:http://cardiophile.org/2009/02/judkins-left-coronary-catheter.html> (3 pages).

Oct. 5, 2011 Notification of Transmittal of the International Search Report and the Written Opinion of the International Searching Authority, or the Declaration for counterpart International Application No. PCT/US2011/040348 (16 pages).

Jul. 19, 2011 Communication in European Application No. 04760155.4 (5 pages).

Translation of Aug. 15, 2007 mailed Japanese Patent Office Action, Application No. 1999-139033 (4 pages).

Australian Patent Examination Report No. 1 for AU Application No. 2011267862 dated Feb. 21, 2013, 3 pages, Australia.

Canadian Office Action for CA Application No. 2,800,920 dated Dec. 2, 2013, 2 pages, Canada.

European Communication Pursuant to Rules 161(1) and 162 EPC for EP Application No. 11726313.7 dated Jan. 22, 2013, Netherlands.

European Search Report for European Application No. 14156617.4-1659 dated May 16, 2014, 6 pages, Munich, Germany.

Russian Office action with English translation for Russian Application No. 2012150415 dated Feb. 20, 2014, 11 pages, Russia.

Notice of Reasons for Rejection with English translation for Japanese Application No. 2013-515433 dated Jan. 28, 2014, 9 pages, Japan.

KIPO's Notice of Preliminary Rejection with English translation for Korean Application No. 10-2012-7032564 dated Feb. 19, 2014, 9 pages, Korea.

Notice of Reasons for Rejection with English Translation for Japanese Application No. 2013-515433 dated Aug. 18, 2014, 7 pages.

KIPO's Notice of Last Preliminary Rejection with English Translation for Korean Application No. 10-2012-7032564 dated Aug. 19, 2014, 3 pages.

Notification of the First Office Action with English Translation for Chinese Application No. 201180029247.0 dated Sep. 1, 2014, 13 pages.

\* cited by examiner

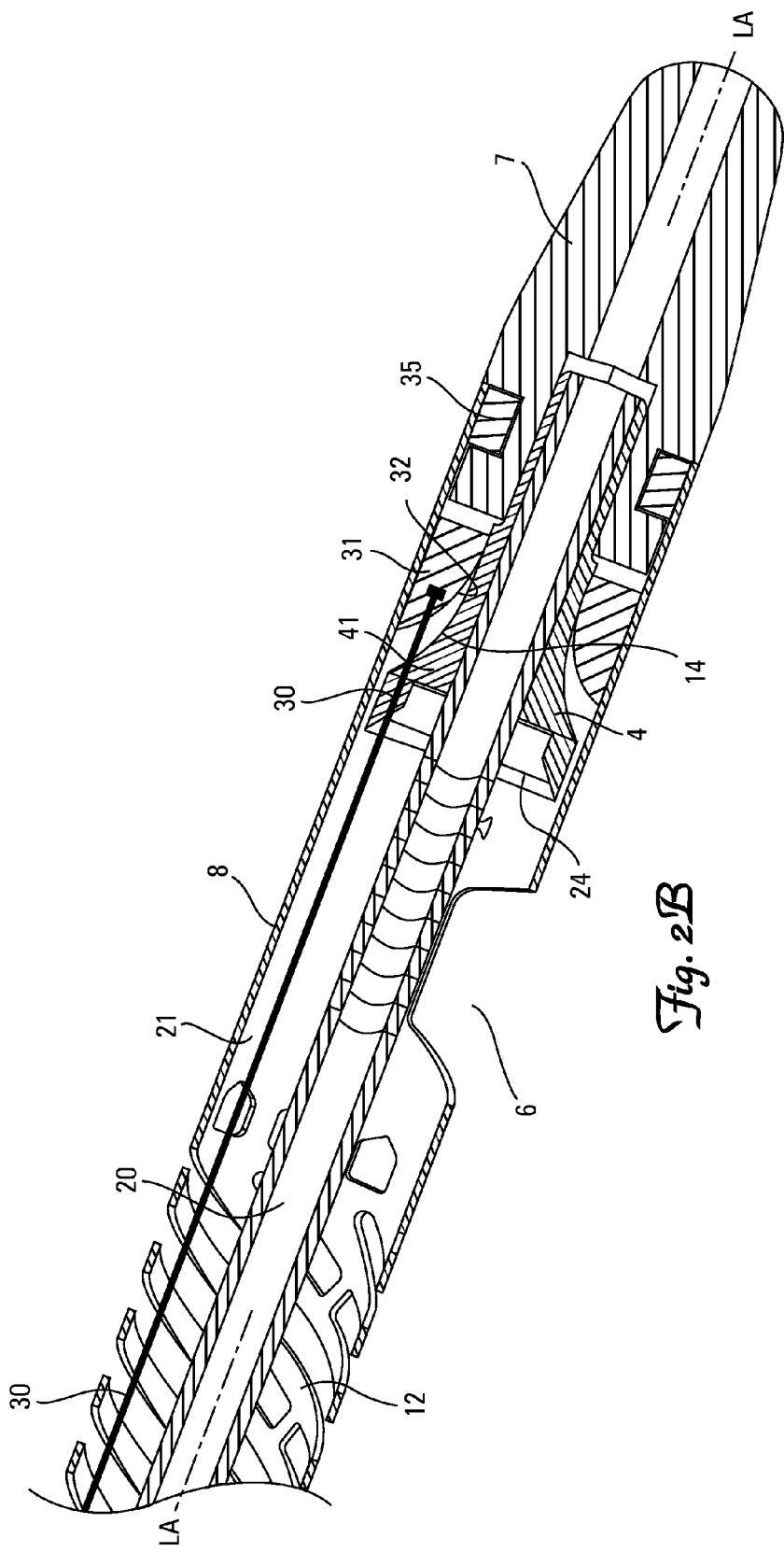

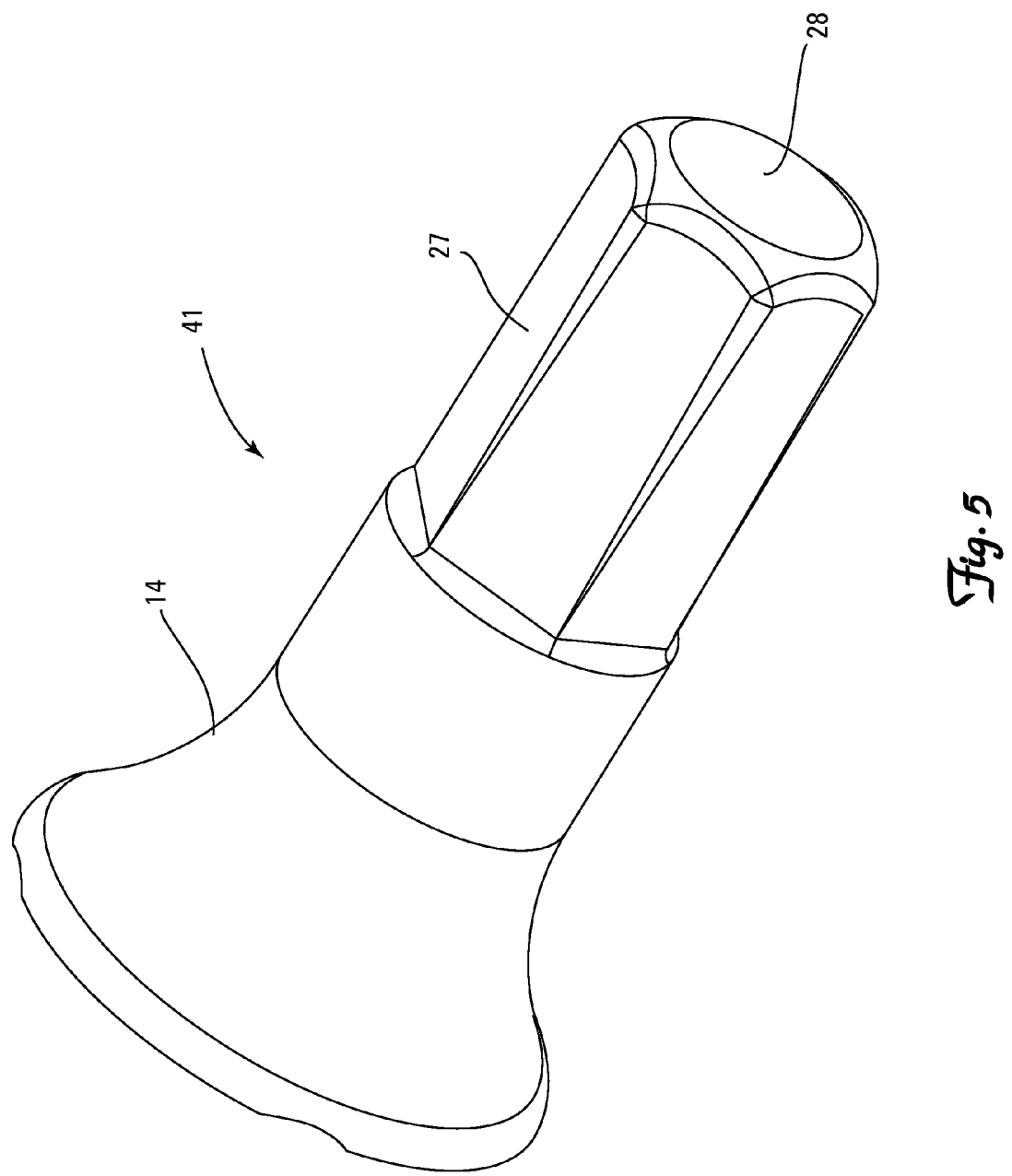

MATERIAL REMOVAL DEVICE AND METHOD OF USE

This application claims the benefit of U.S. Provisional Patent Application No. 61/354,487, filed Jun. 14, 2010, entitled "Material Removal Device and Method of Use", the contents of which are hereby incorporated by reference herein.

FIELD OF THE INVENTION

The present invention relates to catheters used to remove and collect material from a treatment site in a body lumen. More particularly, this invention pertains to catheters capable of crossing a totally occluded treatment site in a vessel to enable the catheter to effectively treat the vessel at the treatment site.

BACKGROUND OF THE INVENTION

Atherosclerosis is a progressive disease of the vascular system whereby atheroma is deposited on the inner walls of blood vessels. Atherosclerosis is a complex, progressive and degenerative condition resulting in the build-up of cholesterol and other obstructive materials, known as plaque, on the walls of the arteries. The accumulation of plaque narrows the interior or lumen of arteries, thereby reducing blood flow.

Plaque occurs in the arteries in several different forms and may be located in many different anatomies throughout the arterial system. Plaque varies in composition, with portions that are hard and brittle, referred to as calcified plaque, and other portions that are fatty or fibrous. Over time atheromatous deposits can become large enough to reduce or occlude blood flow through the vessels, leading to symptoms of low blood flow, such as pain in the legs (on walking or at rest), skin ulcer, angina (at rest or exertional), and other symptoms. To treat this disease and improve or resolve these symptoms it is desirable to restore or improve blood flow through the vessel.

Various means are used to restore or improve blood flow through atheromatous vessels. The atheroma deposits can be displaced by diametrically expanding the vessel by inflating balloons, expanding stents, and other methods. The deposits can be pulverized using lasers and other methods. Atherectomy catheters can be used to remove atheromatous deposits from the blood vessel and may present an ideal solution when the atheromatous debris removed from the vessel is captured and removed from the body.

Many types of atherectomy catheter devices have been proposed, including catheters with rotating burrs, lasers to photodissolve tissue, and cutter-balloon catheters. All have challenges, however, such as traversing through small and tortuous arteries to get to the plaque occluded target zone or zones. This can be especially difficult if the treatment site has been totally occluded by the plaque. Another challenge lies in the inability to safely and efficiently handle and remove the plaque which is removed from the vessel walls during the atherectomy procedure. Some devices are not designed to handle the liberated plaque fragments at all and instead let the fragments migrate through the circulation. This can cause many problems because the liberated plaque remnants can be thrombogenic and can end up causing downstream occlusions. Other catheter designs reduce this problem by capturing the removed plaque in a collection or storage chamber so that it can be removed from the vessel.

One recent atherectomy catheter, the SilverHawk® articulated rotating blade atherectomy catheter, (sold by ev3, Inc.) has been designed to address these problems. The SilverHawk® catheter (features of which are exemplified in U.S. Pat. Nos. 7,771,444; 7,713,279; and 7,708,749 which are incorporated herein by reference in their entirety) uses a unique rotating blade, a side cutting window through which the blade can be extended, and a hinged nose design which can be controlled to cause the catheter to assume a straight position or an angled position. During the cutting procedure the catheter is in the angled position so the side cutting window and cutting blade can be urged against the vessel wall. The SilverHawk® catheter is moved distally through the lesion during the cutting procedure. The SilverHawk® catheter includes a collection chamber located in a distal portion of the catheter nose distal of the cutting window. The cutting blade and cutting window are configured to direct material cut from the vessel wall through the cutting window and into the collection chamber.

Although the SilverHawk® catheter represents a significant advance over prior art devices challenges remain for atherectomy catheters. For example, if the treatment site is a CTO (chronic total occlusion) it might not be possible to cross the lesion with the catheter. CTO's are sometimes comprised of hard, calcified material which is difficult or impossible to cross with either a standard guidewire or atherectomy catheter. If the CTO can not be crossed with the atherectomy catheter to enable it to be placed in a proper treatment position it can not be used to remove material from the treatment site and other, alternative treatments must be used.

Additionally, catheters that remove material, such as the SilverHawk® catheter, may include a collection chamber positioned distally of the cutting window. This requires that the length of the catheter distal of the cutting window be long enough to accommodate the collection chamber. This creates some conflicting design choices. On the one hand, it is desirable for the collection chamber to have a capacity large enough to accommodate a reasonable amount of cut material before the chamber fills and the catheter must be removed. On the other hand, the increased length of the catheter distal to the cutting window necessary to accommodate a sufficiently large collection chamber is disadvantageous in certain applications. For example, if the treatment site or lesion is located in a vessel with a particularly tortuous anatomy or small size there might not be enough accessible vessel space distal to the lesion to accommodate the distal length of the catheter distal of the cutting window. This accessible space distal to the treatment site is sometimes referred to as the "landing zone". In order for the catheter to be used effectively the anatomy of the vessel must be such as to enable the catheter to be advanced far enough to position the cutting window within the treatment site and the distal portion of the catheter, which houses the collection chamber, in the landing zone. Thus, atherectomy catheters may be difficult to use in vessels with short landing zones.

In addition, during the cutting stroke, the atherectomy catheter may be pushed distally by the operator from the proximal end of the catheter through the treatment site with the cutting blade extending through the cutting window. It is possible during this pushing motion for the catheter to encounter resistance due to vessel size or tortuous vessel anatomy. This resistance can make it more difficult for the operator to control the catheter during use. The pushing motion can also compress the shaft of the catheter when resistance is encountered increasing the possibility that the shaft may buckle. If the resistance encountered with the pushing motion is abruptly released the catheter can jump in the distal direction, possibly causing injury to the vessel such as perforation or dissection. When a catheter is pulled proximally through a vessel the catheter body is in tension rather than compression. With tension there tends to be less stored energy, so a sudden release of resistance encountered with the pulling motion results in a lower possibility of jumping.

SUMMARY OF THE INVENTION

The present invention provides an improved atherectomy catheter having features which overcome the problems encountered by prior art devices. In one embodiment, the atherectomy catheter has a rotating distal tip with an abrasive surface enabling the catheter to cut through and cross a CTO. In another embodiment the atherectomy catheter has a cutting window positioned in a side-wall of the catheter and a cutting blade configured to extend through the cutting window and to cut material from the wall of a vessel at a treatment site as the catheter is pulled proximally through the treatment site. In this embodiment the catheter may optionally have a rotating distal tip with an abrasive surface. The catheter includes a collection chamber positioned proximally of the cutting window. The catheter may include means to direct material cut from the treatment site into the collection chamber. The catheters of this invention may also optionally be configured to prevent the drive shaft from blocking or otherwise interfering with the cutting window. In one embodiment the catheter is provided with a cutting element having two cutting structures and two cutting positions.

In one embodiment the invention is a catheter for removing material from a vascular lumen. The catheter comprises a tubular body having proximal and distal ends and a wall defining a lumen, the wall having a side opening positioned proximal of the distal end of the tubular body. A rotatable shaft is disposed within the lumen of the tubular body. A cutting element is coupled to the rotatable shaft, the cutting element having a cutting edge, the cutting element and rotatable shaft being longitudinally moveable within the tubular body between a stored position in which the cutting element is positioned distal of the side opening and a cutting position in which the cutting element is contained within the lumen of the tubular body and longitudinally aligned with the side opening. The catheter further comprises a cutting element exposure member, the cutting element exposure member being longitudinally moveable within the tubular body between a distal position and a proximal position, the cutting element exposure member being configured such that movement of the cutting element exposure member from the distal position to the proximal position when the cutting element is in the cutting position results in movement of the cutting element from the cutting position to an extended position in which a portion of the cutting edge is extended through the side opening beyond an outer diameter of the tubular body. A material collection chamber is positioned within the tubular body at a location proximal of the side opening.

This embodiment of the invention as well as any of the other embodiments disclosed herein may further comprise additional features including a rotatable tip connected to the distal end of the tubular body and a connector assembly for selectively coupling and uncoupling the rotatable tip from the rotatable shaft. The connector assembly may comprise first and second portions, the first portion comprising a portion of the cutting element which is shaped to mechanically interlock with the second portion comprising a portion of the rotatable tip. This embodiment may additionally comprise a guidewire lumen extending through the rotatable shaft, through the cutting element and through the rotating tip such that the catheter is configured as an over the wire catheter. The rotatable tip may comprise an abrasive surface. The catheter may further comprise a handle attached at a proximal portion of the tubular body, the handle including a power source, a motor coupled to the rotatable shaft, and first and second control members, the first control member being coupled to the rotatable shaft, the second control member being coupled to the cutting element exposure member, the first control member being configured to move the cutting element between the stored position and the cutting position, the second control member being configured to move the cutting element exposure member between the distal position and the proximal position. The cutting element exposure member may comprise a pull wire having distal and proximal ends and an arc shaped bushing connected at the distal end of the pull wire, the proximal end of the pull wire being connected to the second control member. Further, the cutting element exposure member may be selectively moveable to control the amount by which the cutting edge is extended through the side opening.

In this embodiment as well as any of the other embodiments described herein the cutting element may be longitudinally moveable within the tubular body to a material compression position located proximal of the side opening, the cutting element being configured to compress material in the material collection chamber when the cutting element is in the material compression position. The cutting element of the embodiments disclosed herein may further comprise a side cutting blade configured to cut material which invaginates the side opening when the cutting element is in the cutting position. The cutting element may be configured such that material from the vascular lumen is cut with the cutting edge when the cutting element is in the extended position and the catheter is moved proximally within the vascular lumen and material is cut with the side cutting blade when the cutting element is in the cutting position and the catheter is moved distally or proximally within the vascular lumen. The cutting element may comprise a proximally oriented cup shaped surface configured to direct material removed from the vascular lumen into the collection chamber This embodiment of the invention as well as the other embodiments disclosed herein may further comprise means to direct material removed from the vascular lumen proximally into the collection chamber and means for preventing the rotatable shaft from blocking the side opening when the cutting element is in the extended position.

In another embodiment the invention is a catheter for removing material from a vascular lumen. The catheter comprises a tubular body having proximal and distal ends and a wall defining a lumen, the wall having a side opening positioned proximal of the distal end of the tubular body. A rotatable shaft is disposed within the lumen of the tubular body. A cutting element is coupled to the rotatable shaft, the cutting element and rotatable shaft together forming a rotatable assembly, the cutting element having a cutting edge, the cutting element and rotatable shaft being moveable within the tubular body between a position in which the cutting element is contained within the lumen of the tubular body and an extended cutting position in which a portion of the cutting edge is extended through the side opening beyond an outer diameter of the tubular body. A material collection chamber is positioned within the tubular body at a location proximal of the side opening. A rotatable tip is connected to the distal end of the tubular body. The catheter includes a connector assembly for selectively coupling and uncoupling the rotatable tip from the rotatable assembly.

This embodiment may be provided with the additional features described above, Additionally, this embodiment may comprise a cutting element exposure member, the cutting element exposure member being longitudinally moveable within the tubular body between a distal position and a proximal position, the cutting element exposure member being configured such that movement of the cutting element exposure member from the distal position to the proximal position when the cutting element is in the position in which the cutting element is contained within the lumen of the tubular body results in movement of the cutting element from the position within the lumen of the tubular body to the extended cutting position. The catheter may include a handle attached at a proximal portion of the tubular body, the handle including a power source, a motor coupled to the rotatable shaft, and a first control member, the first control member being coupled to the rotatable shaft, the first control member being configured to move the rotatable assembly between the uncoupled position and the coupled position.

In a further embodiment the invention is a catheter for removing material from a vascular lumen. The catheter comprises a tubular body having proximal and distal ends and a wall defining a lumen, the tubular body having a first opening at the distal end and a second opening through the wall proximal of the distal end. The catheter includes a first cutting element positioned at the distal end of the tubular body which is configured to cut material from the vessel through the first opening as the catheter is moved distally through the vessel and a second cutting element positioned proximally of the first cutting element which is configured to remove material from the vessel through the second opening as the catheter is moved proximally through the vessel.

In this embodiment the catheter may further comprise a rotatable shaft disposed within the lumen of the tubular body, the second cutting element being coupled to the rotatable shaft, the second cutting element and rotatable shaft together forming a rotatable assembly. The second cutting element may include a cutting edge, the second cutting element and rotatable shaft being moveable within the tubular body between a position in which the second cutting element is contained within the lumen of the tubular body and an extended cutting position in which a portion of the cutting edge is extended through the second opening beyond an outer diameter of the tubular body. The first cutting element may comprise an abrasive rotatable tip. The catheter may include a connector assembly for selectively coupling and uncoupling the rotatable tip from the rotatable assembly. The second cutting element may further comprise a side cutting blade configured to cut material which invaginates the second opening when the second cutting element is in the position in which the second cutting element is contained within the lumen of the tubular body and a material collection chamber positioned within the tubular body at a location proximal of the second opening.

In another embodiment the invention is a catheter for removing material from a vascular lumen. The catheter comprises a tubular body having proximal and distal ends and a wall defining a lumen, the tubular body having a first opening at the distal end and a second opening through the wall proximal of the distal end. The catheter includes a first cutting element positioned at the distal end of the tubular body which is configured to cut material from the vessel through the first opening as the catheter is moved distally through the vessel, a second cutting element positioned proximally of the first cutting element which is configured to remove material from the vessel through the second opening as the catheter is moved proximally through the vessel and a third cutting element which is configured to remove material from the vascular lumen through the second opening when the catheter is stationary within the vessel, when the catheter is moved distally through the vessel and when the catheter is moved proximally through the vessel.

In this embodiment the catheter may further comprise a rotatable shaft disposed within the lumen of the tubular body, the second cutting element being coupled to the rotatable shaft, the second cutting element and rotatable shaft together forming a rotatable assembly. The second cutting element may include a cutting edge, the second cutting element and rotatable shaft being moveable within the tubular body between a position in which the second cutting element is contained within the lumen of the tubular body and an extended cutting position in which a portion of the cutting edge is extended through the second opening beyond an outer diameter of the tubular body. The first cutting element may comprise an abrasive rotatable tip. The catheter may further comprise a connector assembly for selectively coupling and uncoupling the rotatable tip from the rotatable assembly. The third cutting element may comprise a side cutting blade attached to the second cutting element configured to cut material which invaginates the second opening when the second cutting element is in the position in which the second cutting element is contained within the lumen of the tubular body. The catheter may include a material collection chamber positioned within the tubular body at a location proximal of the second opening. The cutting element exposure member may be selectively moveable to control the amount by which the cutting edge is extended through the side opening.

In another embodiment the invention is a method of removing material from a treatment site within a vascular lumen with a catheter having a tubular body, the tubular body having proximal and distal ends and a wall defining a lumen, the wall having a side opening positioned proximal of the distal end of the tubular body, a rotatable shaft disposed within the lumen of the tubular body and a cutting element coupled to the rotatable shaft, the cutting element having a cutting edge, the proximal end of the tubular body being connected to a control handle, the distal end of the tubular body being connected to a rotatable cutting tip. The method comprises advancing the tubular body through the vascular lumen until the rotatable cutting tip is proximal to the treatment site; rotating the rotatable tip while advancing the tubular body distally across the treatment site to position the side opening at a location within or distal to the treatment site; moving the cutting element from a position within the tubular body to an extended cutting position in which a portion of the cutting edge extends through the side opening beyond an outer diameter of the tubular body; and withdrawing the tubular body proximally through the vascular lumen with the cutting element in the extended cutting position to move the cutting edge across the treatment site to cut material from the treatment site.

In this embodiment the catheter may include a connector assembly for selectively coupling and uncoupling the rotatable cutting tip from the rotatable shaft wherein the step of rotating the rotatable tip comprises rotating the rotatable shaft while the rotatable cutting tip is coupled to the rotatable shaft. In this embodiment the step of withdrawing the tubular body proximally with the cutting tip in the extended cutting position is performed while the rotatable cutting tip is uncoupled from the rotatable shaft. In this embodiment the catheter may include a material collection chamber within the tubular body proximal of the side opening and the method may further include moving the cutting element within the tubular body to a position proximal of the side opening to compress cut material within the material collection chamber. In this embodiment the step of moving the cutting element to an extended cutting position may comprise moving the cutting element proximally within the tubular body from a stored position distal of the side opening to a cutting position in which the cutting element is contained within the lumen of the tubular body and longitudinally aligned with the side opening and moving the cutting element radially outwardly from the cutting position to the extended cutting position. The catheter may include a guidewire lumen which extends through the rotatable shaft, through the cutting element and through the rotatable cutting tip and the step of advancing the tubular body through the vascular lumen may comprise advancing the tubular body over a guidewire inserted within the guidewire lumen.

In this embodiment the handle of the catheter may include first and second control members and the step of moving the cutting element to an extended cutting position may comprise manipulating the first control member to move the cutting element proximally within the tubular body from a stored position distal of the side opening to a cutting position in which the cutting element is contained within the lumen of the tubular body and longitudinally aligned with the side opening and manipulating the second control member to move the cutting element radially outwardly from the cutting position to the extended cutting position. Further, the cutting element may have a second cutting edge and the method may further comprise advancing the tubular body distally through the vascular lumen with the cutting element in the extended cutting position to move the second cutting edge across the treatment site to cut material from the treatment site. In this method the step of advancing the tubular body distally through the vascular lumen with the cutting element in the extended cutting position may be performed after the step of withdrawing the tubular body proximally through the vascular lumen with the cutting element in the extended cutting position. The method may further comprise rotating the tubular body about a longitudinal axis of the tubular body to reorient the position of the cutting element within the treatment site.

In a further embodiment the invention is a method of removing material from a treatment site within a vascular lumen with a catheter having a tubular body, the tubular body having proximal and distal ends and a wall defining a lumen, the wall having a side opening positioned proximal of the distal end of the tubular body, a rotatable shaft disposed within the lumen of the tubular body and a cutting element coupled to the rotatable shaft, the cutting element having first and second cutting edges, the proximal end of the tubular body being connected to a control handle. The method comprises advancing the tubular body through the vascular lumen until the side opening is proximal to the treatment site; moving the cutting element from a position within the tubular body to an extended cutting position in which a portion of the first and second cutting edges extend through the side opening beyond an outer diameter of the tubular body; advancing the tubular body distally through the vascular lumen with the cutting element in the extended cutting position to move the first cutting edge across the treatment site to cut material from the treatment site; and withdrawing the tubular body proximally through the vascular lumen with the cutting element in the extended cutting position to move the second cutting edge across the treatment site to cut material from the treatment site.

In this embodiment the step of withdrawing the tubular body proximally through the vascular lumen with the cutting element in the extended cutting position may be performed after the step of advancing the tubular body distally through the vascular lumen with the cutting element in the extended cutting position. The method may further comprise rotating the tubular body about a longitudinal axis of the tubular body to reorient the position of the cutting element within the treatment site.

These and other aspects of the invention will become apparent from the following description of the preferred embodiments, drawings and claims. The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 2B illustrates a cross-sectional view of a distal end portion of the atherectomy catheter illustrated in FIG. 1A with a cutting element in a stored position.

FIG. 5 illustrates a perspective view of a cutter drive adaptor of the present invention.

DETAILED DESCRIPTION

Figure 1A:
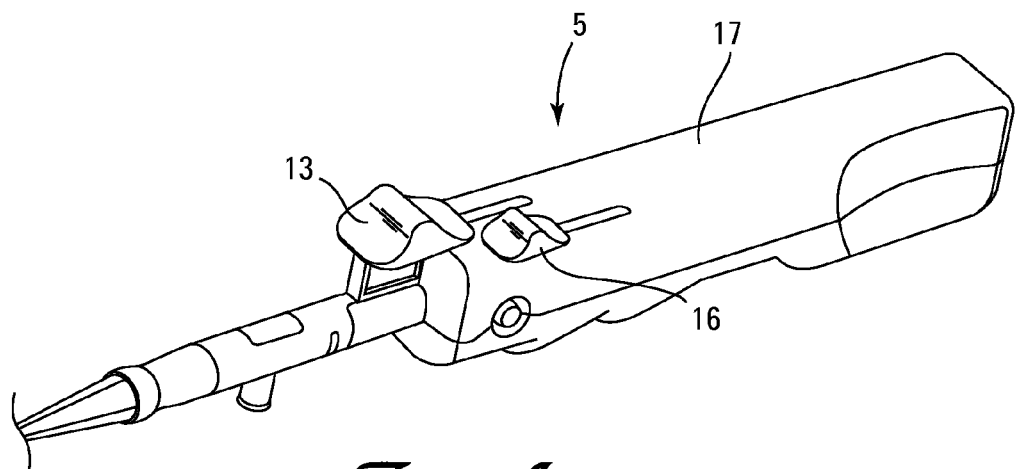
FIG. 1A illustrates a partial side perspective view of a cutter driver of a proximal end of an atherectomy catheter of the present invention.

Apparatus according to the present invention will generally comprise catheters having catheter bodies adapted for intraluminal introduction to the target body lumen. The dimensions and other physical characteristics of the catheter bodies will vary significantly depending on the body lumen which is to be accessed. In the exemplary case of atherectomy catheters intended for intravascular introduction, the distal portions of the catheter bodies will typically be very flexible and suitable for introduction over a guidewire to a target site within the vasculature. In particular, catheters can be intended for "over-the-wire" introduction when a guidewire channel extends fully through the catheter body or for "rapid exchange" introduction where the guidewire channel extends only through a distal portion of the catheter body. In other cases, it may be possible to provide a fixed or integral coil tip or guidewire tip on the distal portion of the catheter or even dispense with the guidewire entirely. For convenience of illustration, guidewires will not be shown in all embodiments, but it should be appreciated that they can be incorporated into any of these embodiments.

Catheter bodies intended for intravascular introduction will typically have a length in the range from 50 cm to 200 cm and an outer diameter in the range from 1 French to 12 French (0.33 mm: 1 French), usually from 3 French to 9 French. In the case of coronary catheters, the length is typically in the range from 125 cm to 200 cm, the diameter is preferably below 8 French, more preferably below 7 French, and most preferably in the range from 2 French to 7 French. Catheter bodies will typically be composed of an organic polymer which is fabricated by conventional extrusion techniques. Suitable polymers include polyvinylchloride, polyurethanes, polyesters, polytetrafluoroethylenes (PTFE), silicone rubbers, natural rubbers, and the like. Optionally, the catheter body may be reinforced with braid, helical wires, coils, axial filaments, or the like, in order to increase rotational strength, column strength, toughness, pushability, and the like. Suitable catheter bodies may be formed by extrusion, with one or more channels being provided when desired. The catheter diameter can be modified by heat expansion and shrinkage using conventional techniques. The resulting catheters will thus be suitable for introduction to the vascular system, including both coronary arteries and peripheral arteries, by conventional techniques.

The side openings or cutting windows of the atherectomy catheters of the present invention may have a length of approximately 2 to 6 mm. In other embodiments, however, the opening or cutting window can be larger or smaller, but should be large enough to allow the cutter to protrude a predetermined distance that is sufficient to cut or debulk material from the body lumen at a treatment site.

Referring to FIGS. 1A to 6, an atherectomy catheter 2 is shown. Catheter 2 has a cutting element 4, which is used to cut material from a blood flow lumen such as an arterial or venous blood vessel. Catheter 2 may include an abrasive rotating tip 7, which is used to bore through any occlusion in a lumen that may otherwise prevent distal movement of the catheter through the vessel and is discussed in greater detail below. It should be noted that the abrasive tip is optional and the atherectomy catheter may be manufactured with no abrasive tip depending upon the application. The cutting element is mounted at the distal end of a flexible drive shaft 20. Drive shaft 20 extends through a lumen 21 in catheter 2. Catheter 2 is comprised of a tissue collection chamber 12. In some embodiments tissue collection chamber 12 is a slotted metallic tube with a covering of polymer such as heat shrink tubing. In other embodiments tissue collection chamber 12 is a length of catheter body 8 located proximal to window 6. Catheter body 8 may be provided with a sidewall opening with tubing attached thereto (neither shown) to facilitate suction of cut debris or injection of fluid (including medications) through the annular space between catheter body and drive shaft 20. Catheter 2 is coupled to at its proximal end to a handle such as exemplary cutter driver 5.

Figure 1B:
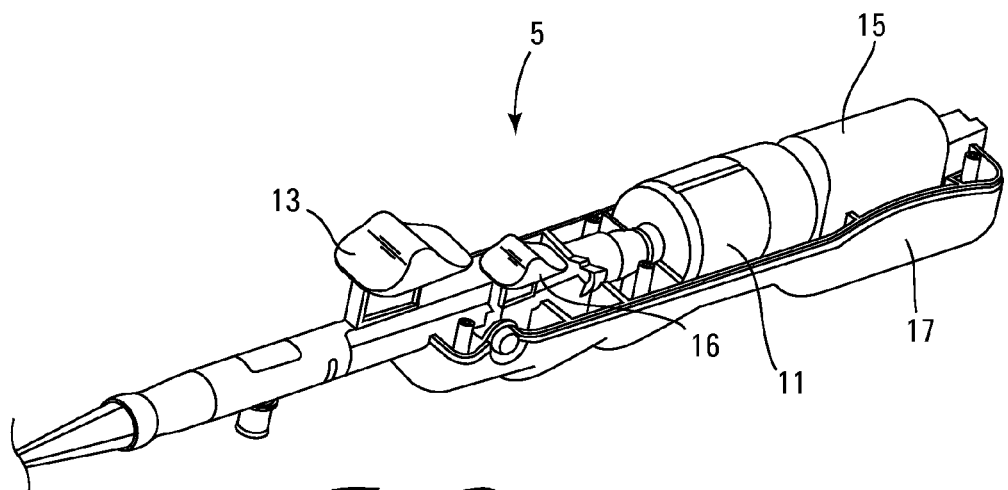
FIG. 1B illustrates a side perspective view of the cutter driver of FIG. 1A with a top housing portion removed.

Cutter driver 5 is comprised of motor 11, power source 15 (for example, one or more batteries), microswitch (not shown), housing 17 (upper half of housing is removed as shown in FIG. 1B), lever 13, lever 16 and connection assembly (not shown) for connecting shaft 20 to driver motor 11. Cutter driver 5 can act as a handle for the user to manipulate catheter 2. Lever 13 moves between a forward, or distal position, and a rearward, or proximal position. Lever 13 is operatively coupled to drive shaft 20 so that advancement or retraction of lever 13 causes corresponding advancement or retraction of drive shaft 20, which in turn controls the position of the cutting element in the housing. As will be discussed in more detail hereafter, when lever 13 is in the forward position cutting element 4 is in its stored position and when lever 13 is in the rearward position cutting element 4 is in its cutting position. Although not shown, cutter driver 5 includes a switch to electrically connect power source 15 to motor 11 thereby causing rotation of cutting element 4. Lever 16 moves between a forward, or distal position, and a rearward, or proximal position. Lever 16 is operatively coupled to a pull wire 30. Pull wire 30 is attached to a bushing 31. As will be discussed in more detail hereafter, lever 16 is in the forward position when the cutting element is in the stored position. When cutting element 4 is moved to its cutting position lever 16 is moved to the rearward position to cause the cutting element to extend through the cutting window.

The cutting element 4 is rotated about a longitudinal axis LA when the shaft 20 rotates. The cutting element 4 is rotated about 1 to 160,000 rpm but may be rotated at any other suitable speed depending upon the particular application. Further description of catheters similar to catheter 2 having cutting elements similar to cutting element 4 are found in U.S. Pat. No. 7,771,444, entitled "Debulking Catheter", the contents of which are incorporated by reference herein.

The cutting element may be formed of one continuous part or may be comprised of multiple parts subsequently joined together by welding, soldering, brazing, adhesive bonding, mechanical interlock or other means. The cutting element includes a cutter drive adaptor 4, which is adapted to receive and connect to the drive shaft, and a cutting edge 22, which is at a radially outer edge 23 of the cutting element 4. The drive shaft may be connected to the cutter drive adaptor by welding, soldering, brazing, or adhesive bonding. Alternatively, the connection may be by mechanical interlock, or other means.

Figure 4A:
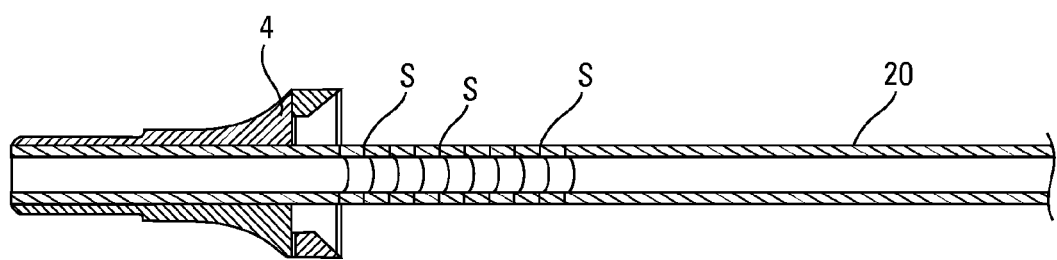
FIG. 4A illustrates a cross-sectional view of an embodiment of a cutting element and drive shaft.
Figure 4B:
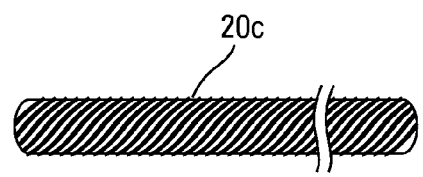
FIG. 4B illustrates a side view of an embodiment of a drive shaft of the present invention.

A perspective view of the cutter drive adaptor is shown in FIG. 5. In FIG. 5 the cutter drive adaptor is shown separated from the rest of the cutting element. In this embodiment drive shaft 20 may be hollow, having a lumen which forms a guidewire lumen. The cutter drive adaptor has an opening configured to receive the distal end portion of the drive shaft. The cutter drive adaptor may include a lumen 28 positioned to align with the guidewire lumen of the drive shaft to allow a guidewire to pass through the cutter drive adaptor. The drive shaft may be made from any suitable material having sufficient flexibility. For example, the drive shaft may comprise braided wires, helically wound wires or a solid tube. In one embodiment as shown in FIG. 4B, drive shaft 20c is made of helically wound stainless steel wires that may be left hand or right hand wound and that have welded proximal and distal ends that do not extend past the outside dimension of the braided steel wires. In some embodiments drive shaft 20c is comprised of multiple layers of helically wound wires, in some cases adjacent layers of helical wound wires are wound with opposite handedness. The guidewire lumen extends from the proximal end to the distal end of drive shaft 20 so that the catheter may be used as an over-the-wire catheter. In a rapid exchange embodiment of the catheter shown in FIG. 16 the catheter is provided with a shortened guidewire lumen. In the rapid exchange embodiment the drive shaft need not have a guidewire lumen and, therefore, may optionally be solid or at least need not be hollow.

By manipulating lever 13 the cutting element 4 is movable, by an operator, between a stored position (FIG. 2B) and a cutting position (FIG. 3) relative to an opening or cutting window 6 in a body 8 of the catheter 2. In the stored position the cutting element is positioned distal to the cutting window within an enclosed distal portion of the catheter. In moving from the stored position to the cutting position the cutting element is moved proximally in a longitudinal or axial direction to a position within the cutting window by moving lever 13 (and drive shaft 20) proximally. As described in more detail hereafter, the cutting element 4 is thereafter moved outwardly relative to the opening 6 so that a portion of the cutting element 4 extends outwardly from the body 8 through the opening 6. More specifically, a portion of the cutting element moves radially outwardly to a position beyond an outer diameter of the catheter body at the location of the cutting window. In one embodiment the cutting element 4 may be positioned relative to the body 8 and opening 6 so that less than 90 degrees of the cutting element 4 is exposed to cut tissue. In other embodiments more or less of the cutting element 4 may be exposed without departing from numerous aspects of the invention.

During use of the catheter, the catheter is advanced through the vessel until opening 6 is positioned adjacent or just distal to the distal end of a treatment site of a vessel with cutting element 4 in the stored position. The cutting element is then moved proximally from the stored position to the cutting position. Once the cutting element has been moved to the proper longitudinal position within the catheter body it is tilted outwardly so that a portion of cutting edge 22 of the cutting element extends beyond a diameter of the catheter housing. The cutting element has a general cylindrical or tubular shape. The cutting edge 22 extends circumferentially around a proximal end of the cutting element and is oriented in a generally proximal direction. Once the cutting element has been thus extended the catheter 2 is pulled proximally through the vessel with the cutting element 4 in the working or cutting position as described in further detail below. As the catheter 2 moves through the blood vessel with the cutting element 4 in the working or cutting position the tissue material is cut by the cutting edge of cutting element 4 and is directed into a tissue collection chamber 12 positioned proximal to the cutting element 4. The tissue collection chamber 12 may be somewhat elongated to accommodate the tissue which has been cut. As mentioned previously, the catheter body 8 may be provided with a side wall opening at a proximal location which can be connected by tubing to a suction source so that debris created by the rotating cutter element 4 can be aspirated through the annular space between the catheter body and drive shaft 20. The tissue collection chamber may be as long as the catheter length which is proximal to the window. The proximal portion of the catheter body may additionally have a sidewall opening or port (not shown) so tissue transported through the catheter can exit through the sidewall port. However, since the tissue collection chamber is positioned proximal of the cutting window its length is not constrained by the size of the landing zone of the treatment site. Therefore, the tissue collection chamber 12 can be made to have any desired length.

Figure 2A:
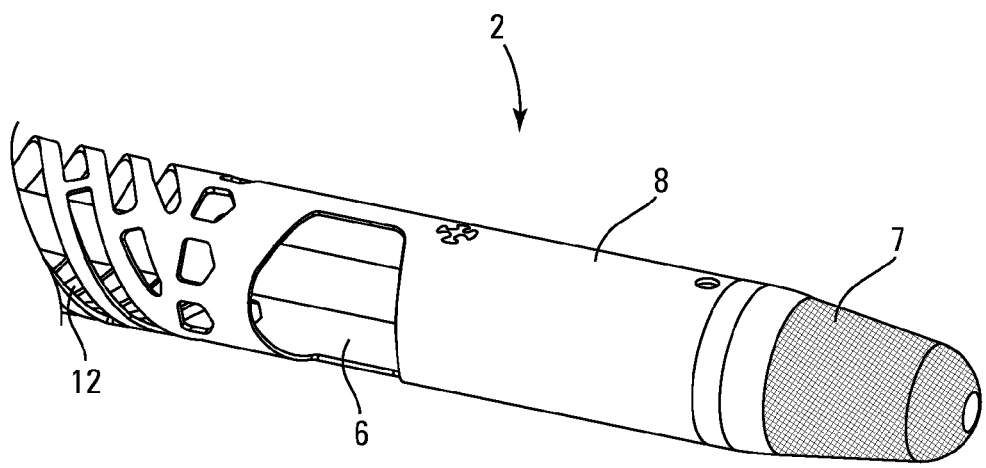
FIG. 2A illustrates a perspective view of a distal end portion of the atherectomy catheter of the present invention.
Figure 3:
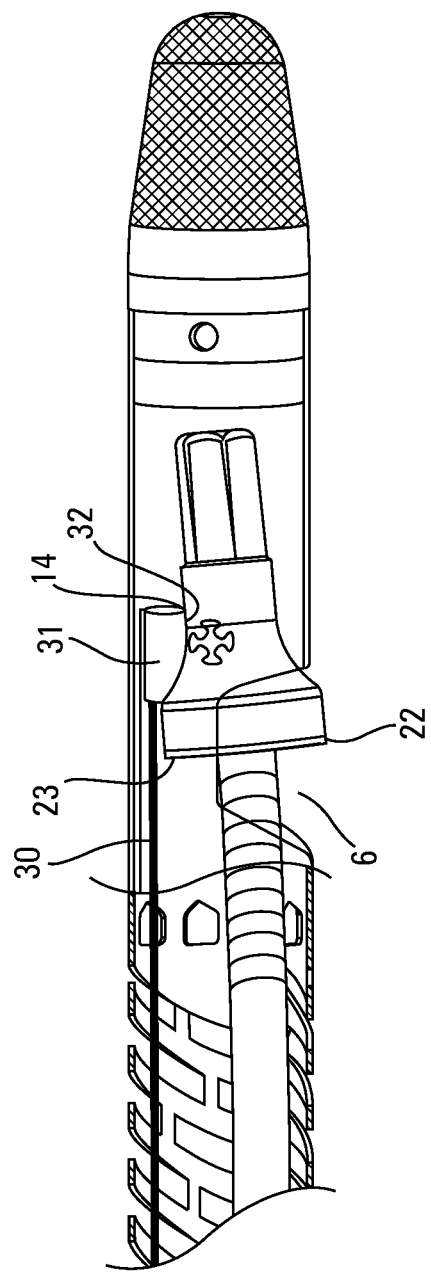
FIG. 3 illustrates a perspective partially cross-sectional, partially translucent view of a portion of the atherectomy catheter illustrated in FIG. 2A with a cutting element in a working position.

Cutting element 4 is exposed through opening 6 through the use of a cutter blade exposure mechanism comprising a pull wire 30 attached to a bushing 31. As best seen in cross-section in FIG. 2B, bushing 31 has a curved or cam surface 32. When the treatment site has been reached, opening 6 is positioned just distally of the lesion to be treated. Lever 13 is then moved proximally to its rearward position to move the drive shaft and cutting element proximally to a position within the cutting window. To expose the cutting element through the cutting window, lever 16 is moved proximally to its rearward position so that pull wire 30 is withdrawn proximally by the operator while the catheter body and cutting element 4 are maintained in a stationary position. As the pull wire 30 is withdrawn, cam surface 32 of bushing 31 acts against an angular ramp surface 14 of cutter drive adaptor 41, causing the cutting element to tilt outwardly so that the cutting edge 22 of the cutting element extends beyond the outer surface of the catheter housing and through opening 6, as shown in FIG. 3. The distance by which cam surface 32 is moved in the proximal direction with respect to ramp surface 14 of the cutter drive adapter 41 determines the distance that the cutting edge extends beyond the outer surface of the catheter. If pull wire 30 is withdrawn a further distance proximally, cam surface 32 of bushing 31 will move further proximally and act on the ramp surface 14 of the cutter drive adaptor 41 to cause it to tilt outwardly at a greater angle so that the cutting edge 22 extends a further distance through opening 6. The amount or distance that cutting edge 22 extends through opening 6 determines the cutting depth of the material removed from the lumen during the procedure. The cutting depth can be controlled by careful manipulation of lever 16 so that diseased tissue can be removed from the treatment site at a preselected cut depth. To facilitate precise control of lever 16 it can be equipped with a ratchet and pawl mechanism, or can be threadably engaged with the handle, or otherwise configured to allow incremental movement and/or positional locking of bushing 31. Pull wire 30 may comprise a metallic wire or other suitable material and may have a substantially constant diameter. Alternatively, pull wire 30 may have a flattened or arcuate cross-section. Pull wire 30 may be contained in lumen 21 of catheter 2 or may be housed in a separate lumen (not shown) within catheter 2. Bushing 31 may have an arcuate cross-sectional shape extending within lumen 21 of catheter 2 for 180 degrees, or less so that it does not interfere with the extension of the cutting element through the opening.

Figure 17A:
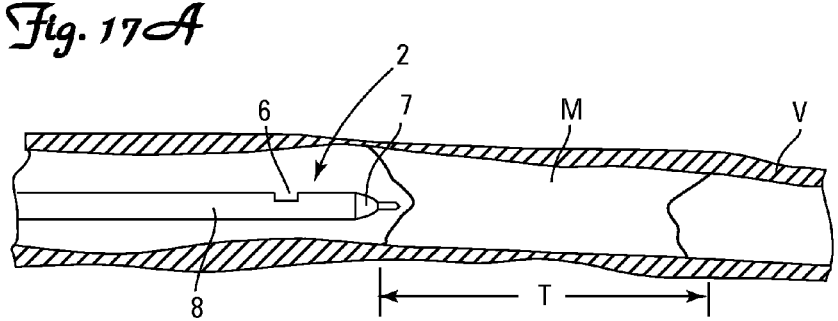
FIGS. 17A, 17B and 17C illustrate the method of using the atherectomy catheter.
Figure 17B:
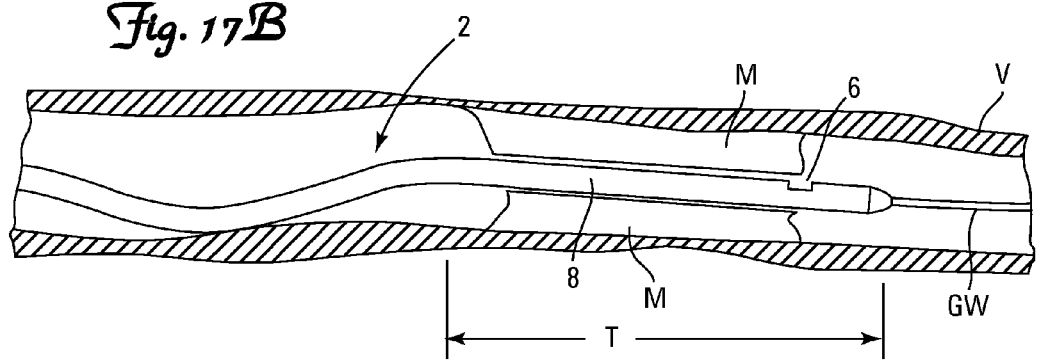
Figure 17C:
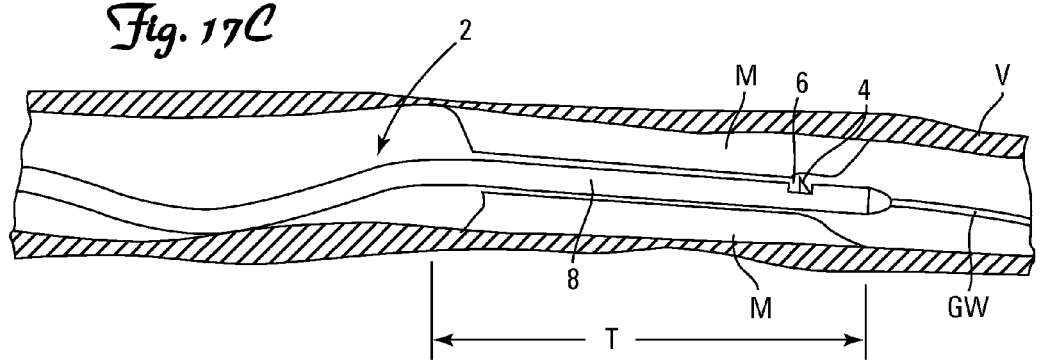

Once the cutting element 4 has been extended into opening 6, the drive motor is engaged to rotate the cutting element (through drive shaft 20) and catheter 2 is proximally withdrawn through the lumen of the vessel to remove material from the lesion. As best seen in FIGS. 17A to 17C, catheter 2 may also comprise a rigid bend or curved shape towards the distal end which may help urge the cutting window 6 and cutting element 4 toward a wall of a body lumen to enhance treatment. Such a rigid bend increases the working range of the catheter by allowing the cutter to be urged against a lumen wall across a wider diameter lumen.

The cutting element 4 may have a cup-shaped surface 24, which directs the tissue cut by the cutting edge 22 into tissue chamber 12. Cutting edge 22 may be at a radially outer edge 23 of the cutting element 4. In some embodiments the cup-shaped surface 24 may be a smooth and continuous surface free of through holes, teeth, fins or other features, which disrupt the smooth nature of the surface 24 for at least half the distance from the longitudinal axis LA to the outer radius at the cutting edge 22. In other embodiments the cup shaped surface may have a limited amount of through holes, teeth, fins or other features. Catheters having cutting elements similar to cutting element 4 are found in U.S. patent application Ser. No. 12/768,281 to Moberg et al., entitled "Methods and Devices for Cutting and Abrading Tissue", published as U.S. Patent Application U.S. 2010/0312263, the contents of which are incorporated herein by reference.

Figure 6:
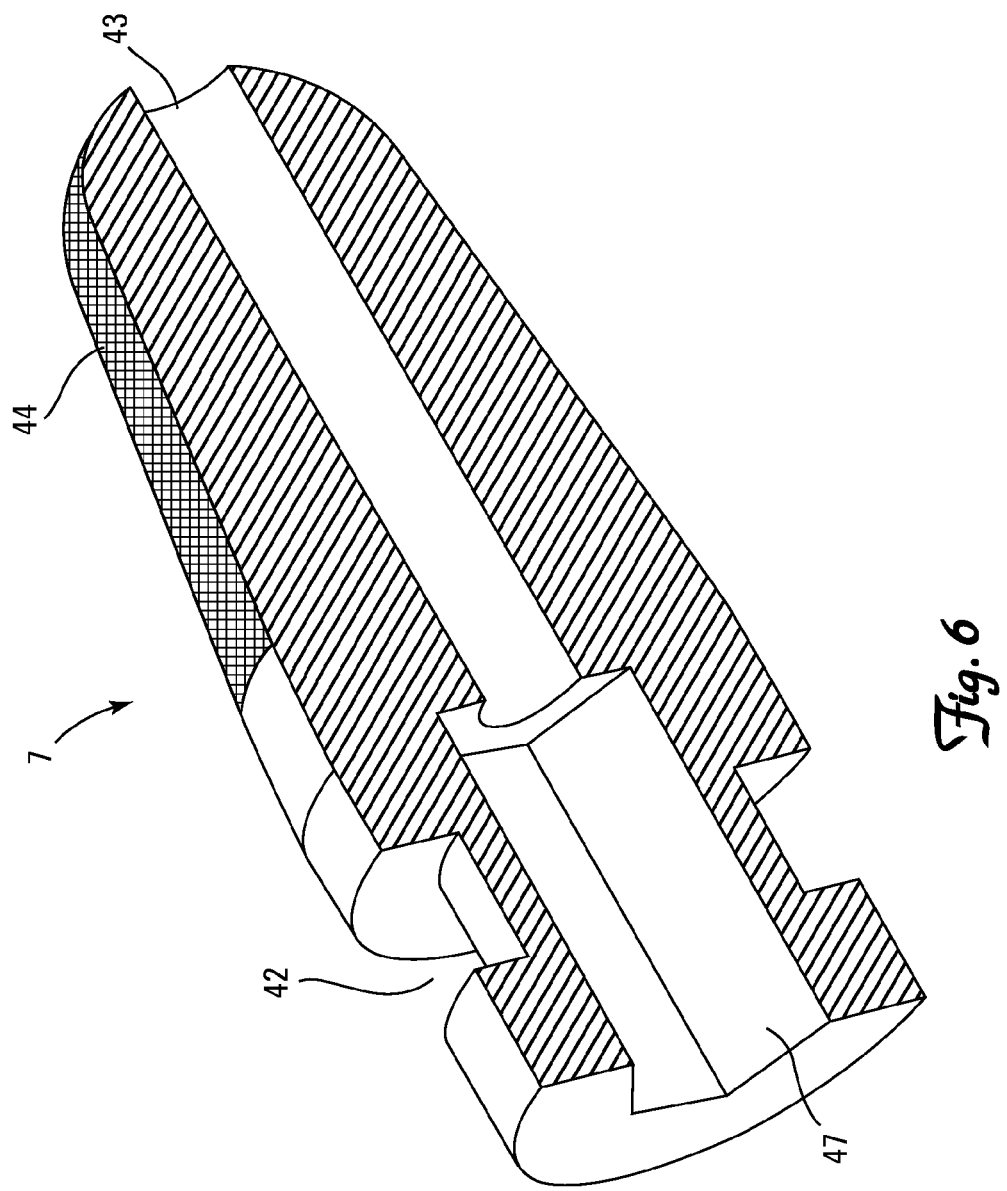
FIG. 6 illustrates a perspective view of a rotating tip element of the present invention.

FIG. 6 is a perspective cross-sectional view of optional rotating tip 7. Any of the catheter embodiments disclosed herein may be provided with either a stationary tip or a rotating tip depending on the application. As previously described, the drive shaft 20 is connected or in some manner coupled to cutter drive adapter 41 to form a rotatable assembly. FIG. 5 is a perspective view of the cutter drive adaptor 41 of cutting element 4. Cutter drive adaptor 41 has a hexagonal male portion 27. The hexagonal male portion of the cutter drive adapter 41 mates with a female hexagonal adapter socket 47 of rotating tip element 7 (as shown in FIG. 2B) to couple the rotating tip to the rotatable assembly when the cutting element 4 is in the stored position. When the cutting element is in the cutting position the rotatable tip is uncoupled from the drive assembly. In other words, the mating portions of the cutter drive adaptor (drive assembly) and the rotatable tip form a connector assembly for selectively coupling and uncoupling the rotatable tip from the rotatable assembly. The stored position is achieved by moving lever 13 to the forward position. When the drive shaft is rotated while the cutting element is in the stored position the rotational motion is imparted to the cutter drive adaptor which, in turn, rotates the rotating tip 7. Rotating tip 7 includes an optional lumen 43 extending from socket 47 to its distal end. Lumen 43 aligns with lumen 28 of the cutter drive adaptor when the cutting element is in the stored position to accommodate a guidewire. Thus, the guidewire lumen for this over-the-wire type catheter comprises the internal lumen of the hollow drive shaft, lumen 28 of the cutter drive adaptor and lumen 43 of the rotating tip. It should be recognized that although the mating portions of the cutter drive adaptor and tip are shown in this embodiment as being hexagonal in cross-section, other cross-sectional shapes such as square, triangular and the like could also be chosen, so long as the mating relationship between the parts is rotationally secure. It should also be recognized that in embodiments of the catheter having a stationary tip the cutter drive adaptor can be modified to not include the hexagonal male portion or any other structure which mates with the tip.

Rotating tip 7 is coupled to the catheter housing by a retention collar 35. Retention collar 35 is fixedly attached to the catheter body 8 by means of rivets, welding, adhesive and the like. Retention collar 35 is accepted in a retention cavity 42 of rotating tip element 7. Retention collar 35 prevents axial movement of rotating tip 7 while at the same time allowing free rotational movement of the tip. When the cutting element is in the stored position and the cutter drive motor is energized to rotate drive shaft 20, the hexagonal male portion 27 of cutter drive adapter 41, which is accepted into the adapter socket 47 of the rotating tip element 7, also rotates, thus rotating the abrasive rotating tip 7. Retention collar 35, which is accepted into the retention cavity 42, allows the rotating tip element 40 to freely rotate while maintaining a secure attachment of the rotating tip element 40 to the catheter 2.

The outer distal surface of the rotating tip element 7 may have a roughened abrasive surface 44 which may be comprised of hard, particulate materials such as diamond, silicon carbide, aluminum oxide, tungsten carbide, metal, hardened steel or other materials, having a range of particle sizes and may be defined by grit size. Abrasive cutting surfaces similar to and suitable for use as abrasive surface 44 are found in U.S. patent application Ser. No. 12/768,281 to Moberg et al., entitled "Methods and Devices for Cutting and Abrading Tissue", published as U.S. Patent Application U.S. 2010/0312263, the contents of which are incorporated herein by reference. During use, as the catheter is distally advanced through the lumen of the vessel, an occlusion or blockage such as a chronic total occlusion (CTO) may prevent the catheter from progressing. In this instance the rotating tip 7 would be engaged and begin to rotate and the roughened abrasive surface 44 would begin to shear away layers of the CTO, or other blockage, until the rotating tip 7 bores through the CTO (or other blockage) enabling the catheter 2 to be advanced to position the cutting window at a location allowing material to be removed by the cutting element from the lesion at the treatment site. As mentioned previously, the catheter body may be provided with a side wall opening at a proximal location which can be connected by tubing to a suction source so that debris created by the rotating tip can be aspirated through the annular space between the catheter body and the drive shaft.

In use, catheter 2 cuts softer atheroma from a vessel wall in relatively large strips and cup shaped surface 24 directs these strips through opening 6 into collection chamber 12. Since collection chamber 12 is positioned proximal of window 6 and cutting element 4 it is desirable to keep the passageway between window 6 and the collection chamber as free from obstruction as possible. One potential obstruction which could hinder the movement of cut material from the window to the collection chamber is the drive shaft. As explained above, the cutting element is tilted in the direction of the window in order to extend the cutting edge out of the window during the cutting procedure. This tilt also affects the position of the drive shaft and tends to redirect a portion of the drive shaft just proximal to the cutting element in the direction of the window. The amount of obstruction caused by this deflection of the drive shaft when the cutting element is tilted is minimized by making the drive shaft extremely flexible over its length or, in another embodiment, over the length of the drive shaft immediately proximal to the cutter. For example, a flexible drive shaft will bend sharply adjacent its connection or coupling point with the cutting element so that it maintains a position close to the central axis of the catheter 2. Increased flexibility of drive shaft 20 also reduces any resistive force of the drive shaft to the angular tilt the cutting element 4. In drive shafts formed from solid hollow tubular material the drive shaft may be provided with spiral (or otherwise directed) cuts S performed mechanically by a laser as seen in cross section in FIG. 4A. In some embodiments the spiral cuts are made in a direction that tightens when the shaft is rotated and make connecting shaft 20 more flexible along the spiral cut portion just proximal to the coupling point with cutting element. These spiral cuts allow the cutting element to tilt freely outside opening 6 while the position of the drive shaft 20 may be maintained within the housing and out of the way of material being cut by cutting element 4 and directed into collection chamber 12.

Figure 13:
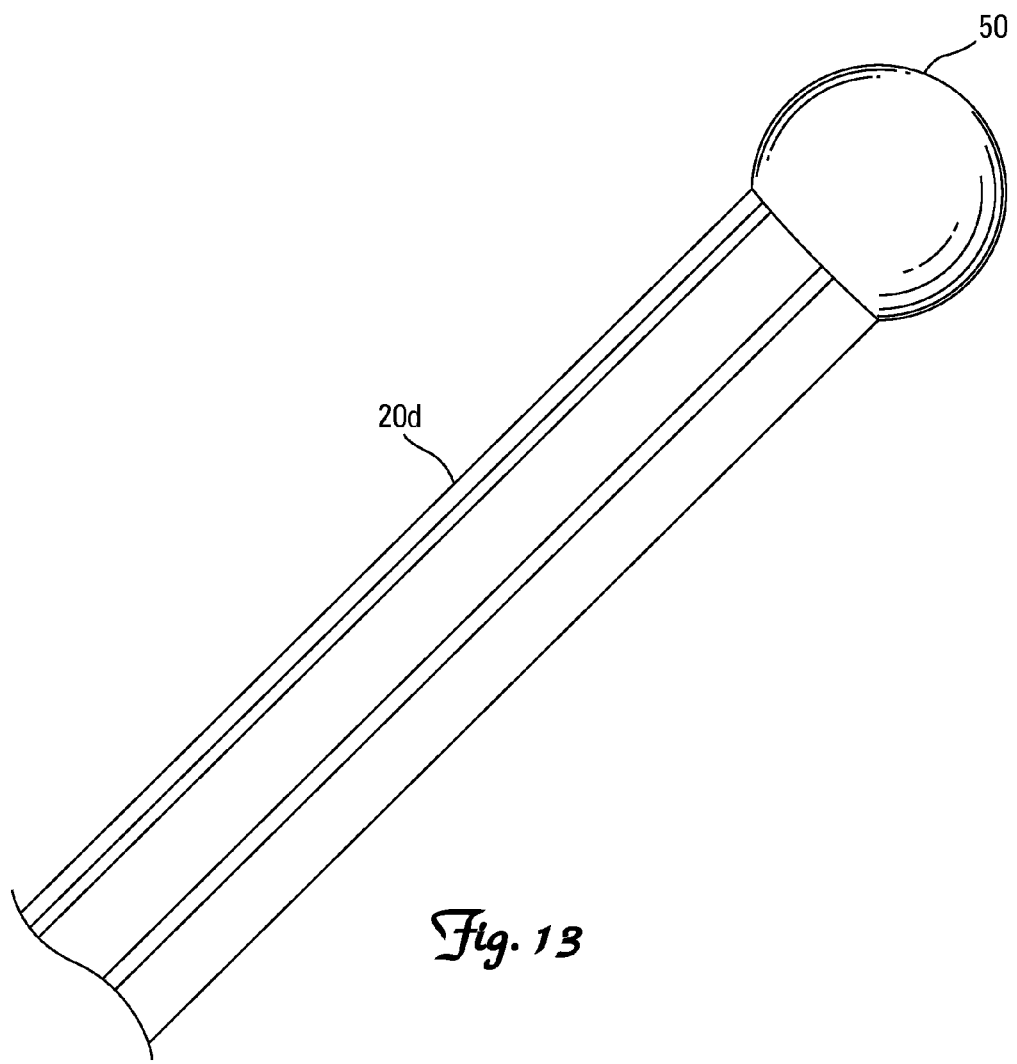
FIGS. 13 to 15 illustrate an alternative embodiment of the drive shaft and cutter drive adaptor.
Figure 14:
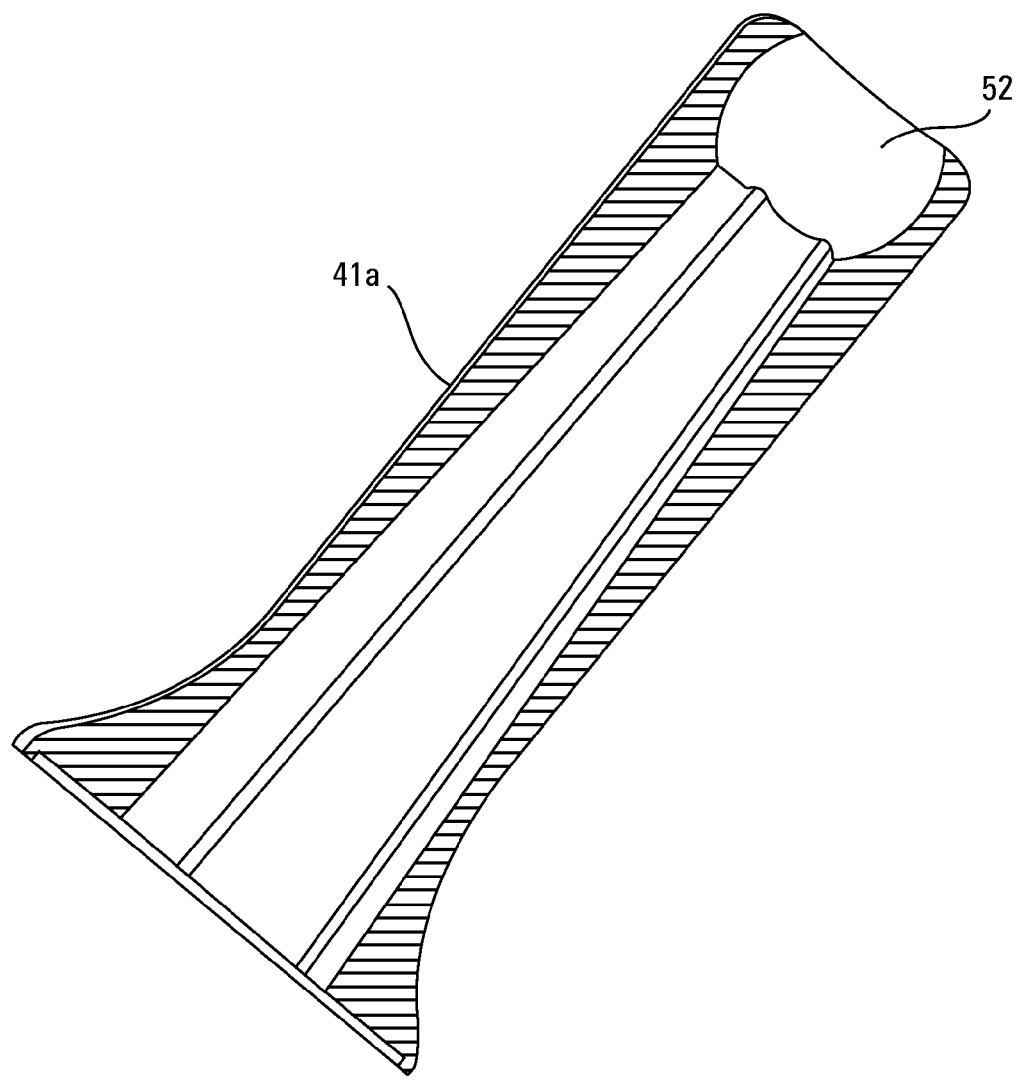
Figure 15:
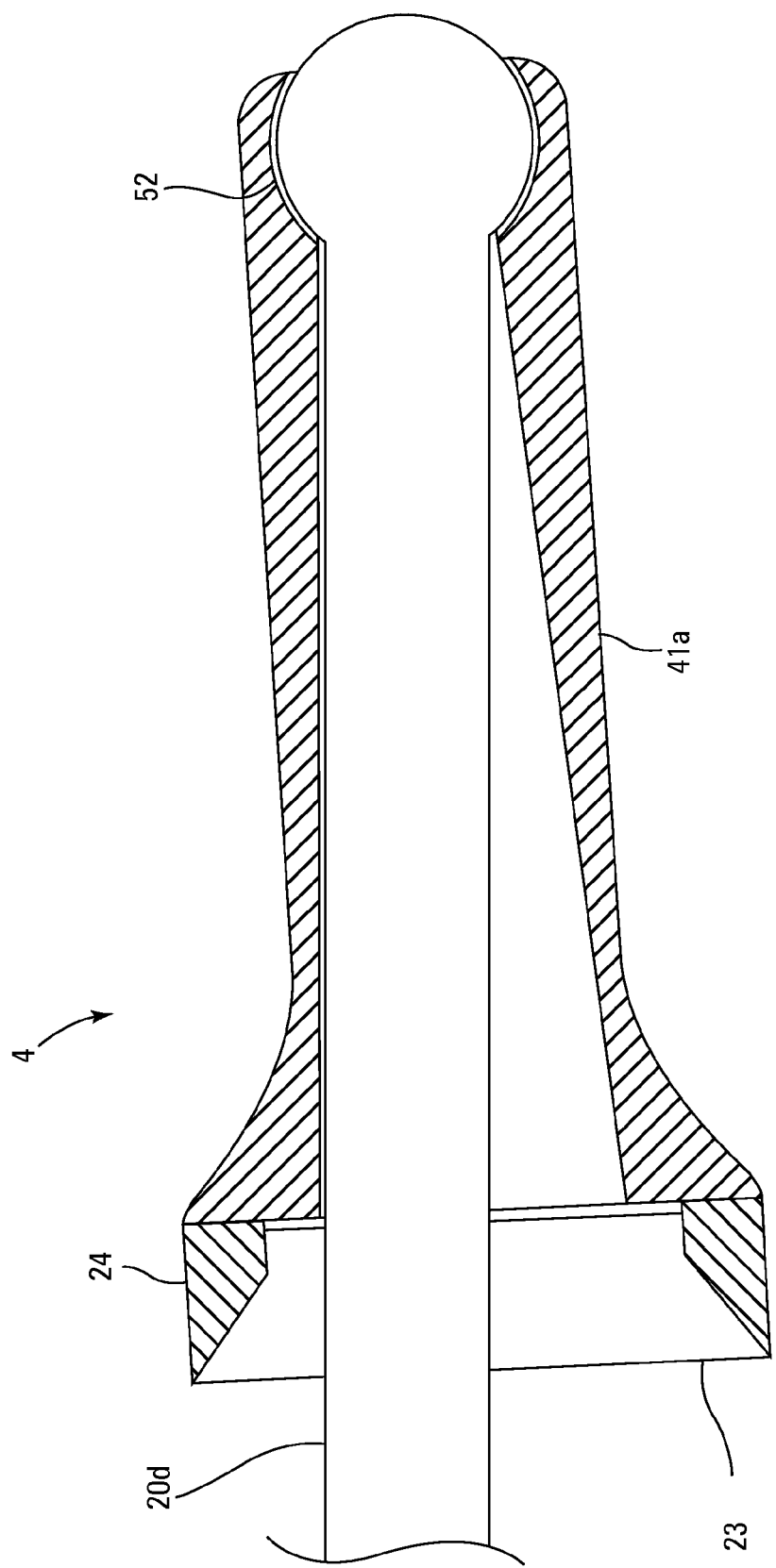

In an alternative embodiment shown in FIGS. 13 to 15 the drive shaft and cutting element may be modified to further ensure that the drive shaft does not obstruct the passageway between the window and the collection chamber. FIG. 13 shows an alternative drive shaft 20d which has an enlarged ball 50 at its distal end. FIG. 14 shows an alternative cutter drive adaptor 41a having a socket 52 at its distal end shaped to receive the enlarged ball 50 of drive shaft 20d. FIG. 15 is a cross-sectional view of drive shaft 20d coupled to cutter drive adaptor 41a. A distal region of drive shaft 20d adjacent enlarged ball 50 has a hexagonal cross-sectional shape. Cutter drive adaptor 41a includes a lumen which tapers inwardly from the proximal end to socket 52. The tapering shape is configured to match the cross-sectional shape of the drive shaft adjacent the enlarged ball. In this embodiment the connection between the drive shaft and the cutter drive adaptor is mechanical. Ball 50 is securely retained within socket 52 and prevents any longitudinal movement of the drive shaft with respect to the cutter drive adaptor. The tapered internal sides of the cutter drive adaptor are sized to prevent the drive shaft from rotating with respect to the cutter drive adaptor. However, the tapered internal sides of the cutter drive adaptor are sized to allow some pivoting movement of the drive shaft with respect to the cutter drive adaptor. This configuration allows the cutter drive adaptor 41a to receive and be rotated by drive shaft 20d while at the same time permitting the cutter drive adaptor to tilt or pivot about enlarged ball 50. Thus, in this embodiment, when cutter drive adaptor 41a is tilted towards the cutting window to expose the cutting element through the window in the manner previously described, the drive shaft is configured to remain centered within the catheter body or is at least not urged toward the window to a substantial degree. This embodiment thus reduces potential interference of the drive shaft with cut material passing from the cutting window to the collection chamber.

Figure 7:
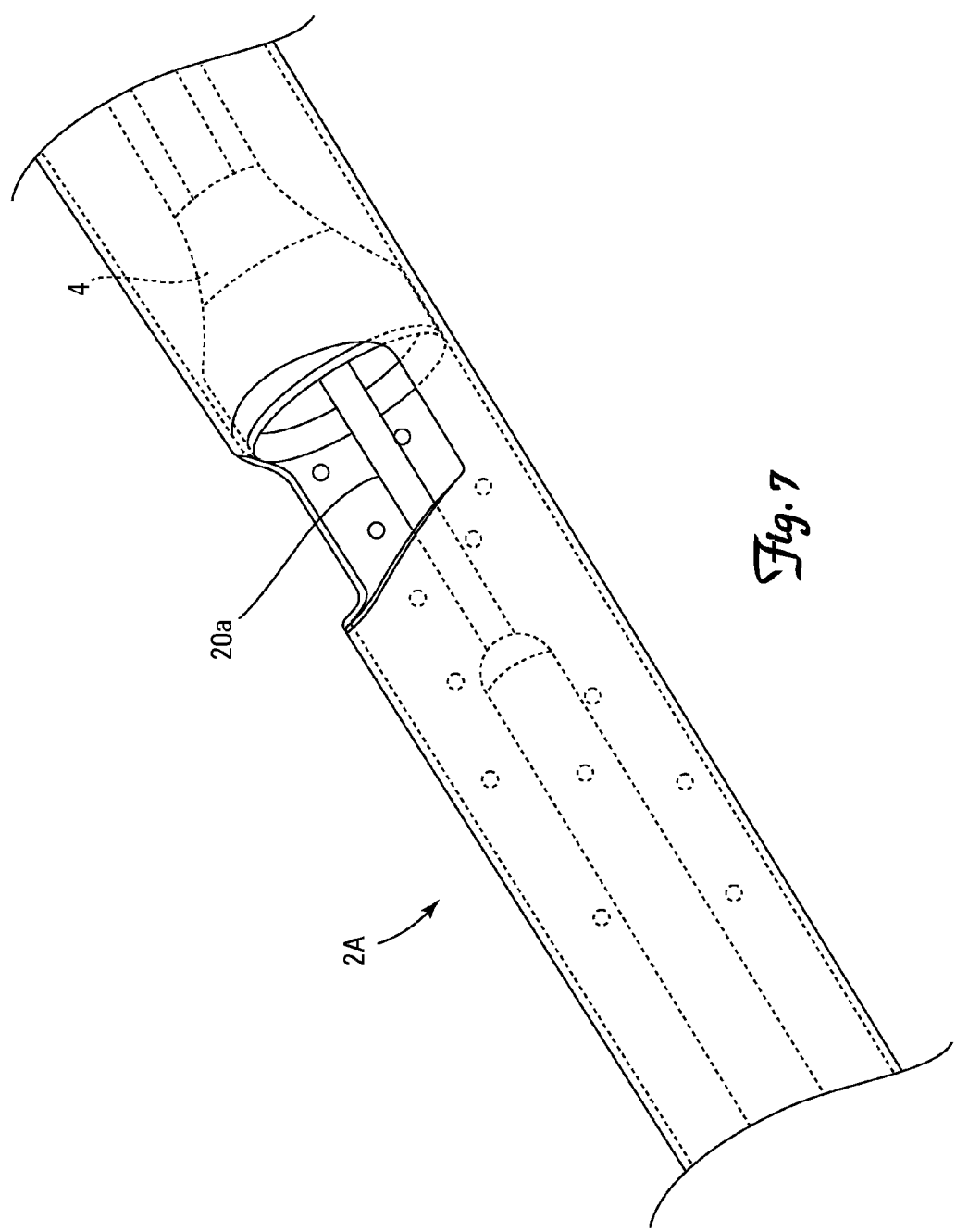
FIG. 7 illustrates a partial translucent side view of a portion of the catheter with an alternate embodiment of the drive shaft.
Figure 8:
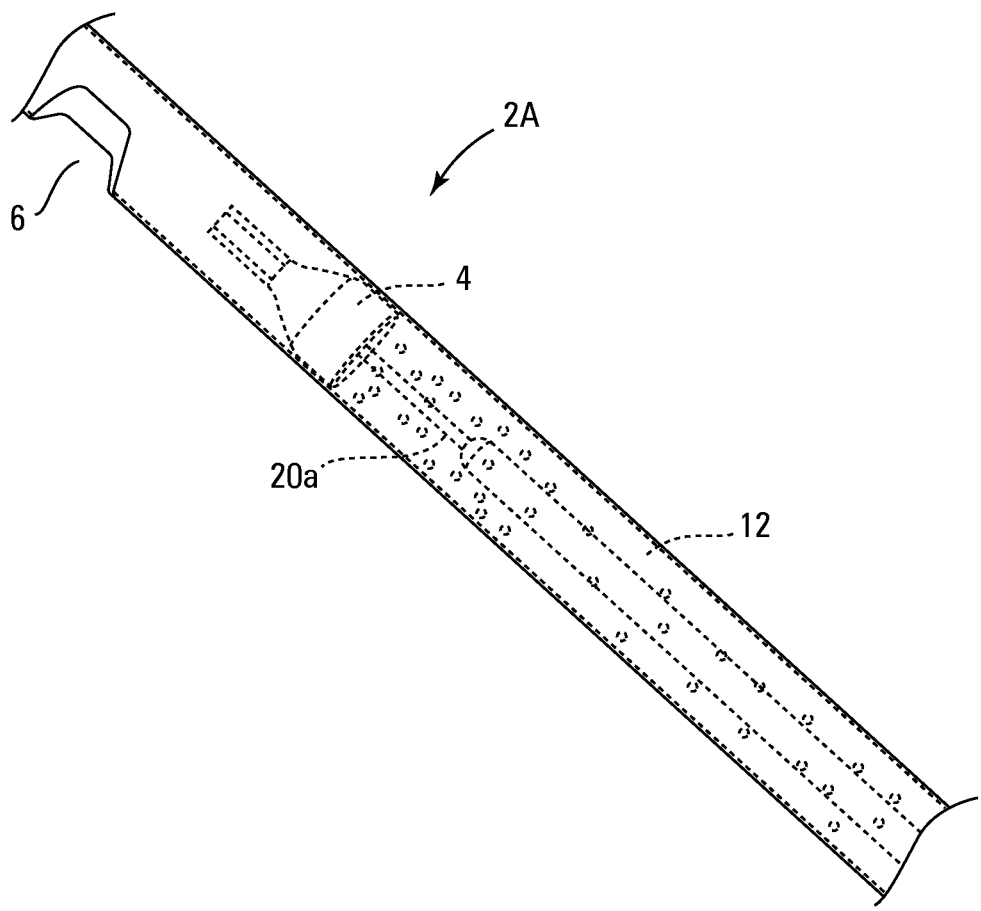
FIG. 8 illustrates a partial translucent side view of the embodiment of FIG. 7 having an improved material collection feature.

An alternative catheter embodiment is shown in FIGS. 7 and 8. Catheter 2A is shown wherein the same or similar reference numbers of catheter 2A refer to the same or similar structures of catheter 2 and all discussion concerning the same or similar features of catheter 2 are equally applicable here unless noted otherwise. Compared to catheter 2, drive shaft 20a has been given a narrowed diameter immediately proximal to the cutting element 4. This narrowed diameter presents less obstruction to the passage of material from cutting window 6 to collection chamber 12. Thus, catheter 2A allows for greater ease of collecting atheroma/tissue at a treatment site by providing additional space for the atheroma/tissue to be collected inside the catheter. It should be noted that the drive shaft 20a (or the drive shafts of any of the other embodiments disclosed herein) could be additionally coated with a lubricant or Teflon to reduce atheroma/tissue from sticking to the drive shaft 20a.

FIG. 8 shows catheter 2A which is provided with features that enhance the material storage efficiency of the collection chamber. In this embodiment the handle or control mechanism is modified to allow the drive shaft to be withdrawn further proximally resulting in the cutting element being withdrawn proximally past the cutting window. In this embodiment lever 16 is advanced distally thereby advancing bushing 31 distally and allowing cutting element 4 to return within the catheter body so the cutting element does not extend through the cutting window. The drive shaft and cutting element 4 are then pulled back proximally toward the operator while the catheter and housing remain stationary. When the cutting element is pulled back proximally past the cutting window the cup shaped surface 24 collects and pulls back the atheroma/tissue within the lumen of the catheter into the collection chamber 12. This compresses the atheroma/tissue and adds further material storage capability to catheter 2A. The pull back compression step can be done while the cutting element is being rotated although it will typically be done without rotation of the cutting element. It should be noted that this pull back compression system could be incorporated into any of the catheter embodiments disclosed herein for the purpose of increasing the storage efficiency of the collection chamber.

Figure 9:
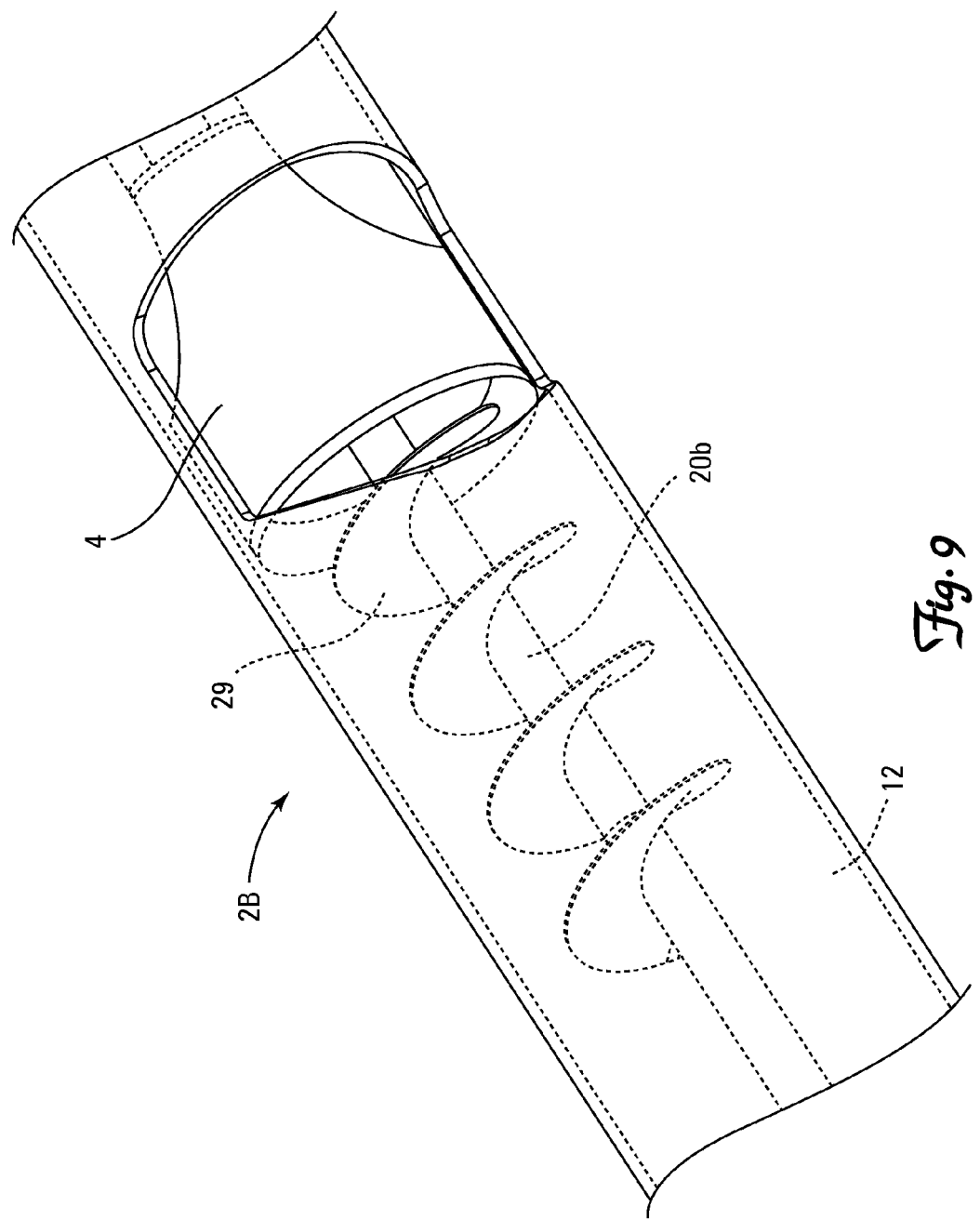
FIG. 9 illustrates a partial translucent side view of a portion of the catheter with an alternate embodiment of the drive shaft.

Another embodiment of the catheter is shown in FIG. 9. Catheter 2B is shown wherein the same or similar reference numbers of catheter 2B refer to the same or similar structures of catheter 2 and all discussion concerning the same or similar features of catheter 2 are equally applicable here unless noted otherwise. Compared to catheter 2, drive shaft 20b has been provided with auger blades 29 immediately proximal to the cutting element 4. As the auger blades 29 rotate along with drive shaft 20b, atheroma/tissue entering the cutting window is pulled away from the cutting area and treatment site and into the collection chamber 12 of catheter 2B. This embodiment provides greater ease of collecting atheroma/tissue at a treatment site by providing additional space for the atheroma/tissue to be collected inside the catheter. It should be noted that the connecting shaft 20b and auger blades 29 could be additionally coated with a lubricant or Teflon to reduce atheroma/tissue from sticking to the drive shaft 20b. In this embodiment the cutting element may be elongated and have the features of cutting element 4c described below in connection with FIGS. 10 to 12. As discussed previously, suction may be provided through catheter 2 to assist with drawing material proximally from the cutter element to auger blades 29.

Figure 10:
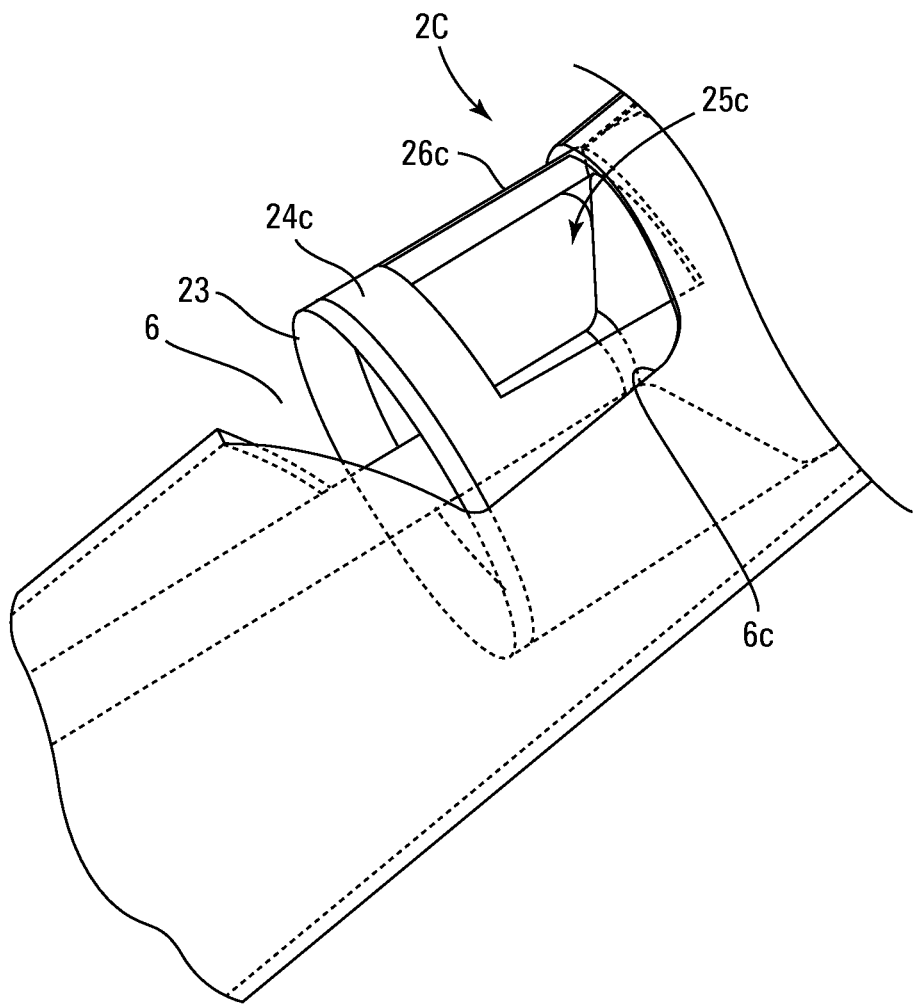
FIGS. 10 to 12 illustrate partial translucent side views of an alternate embodiment of a cutting element.
Figure 11:
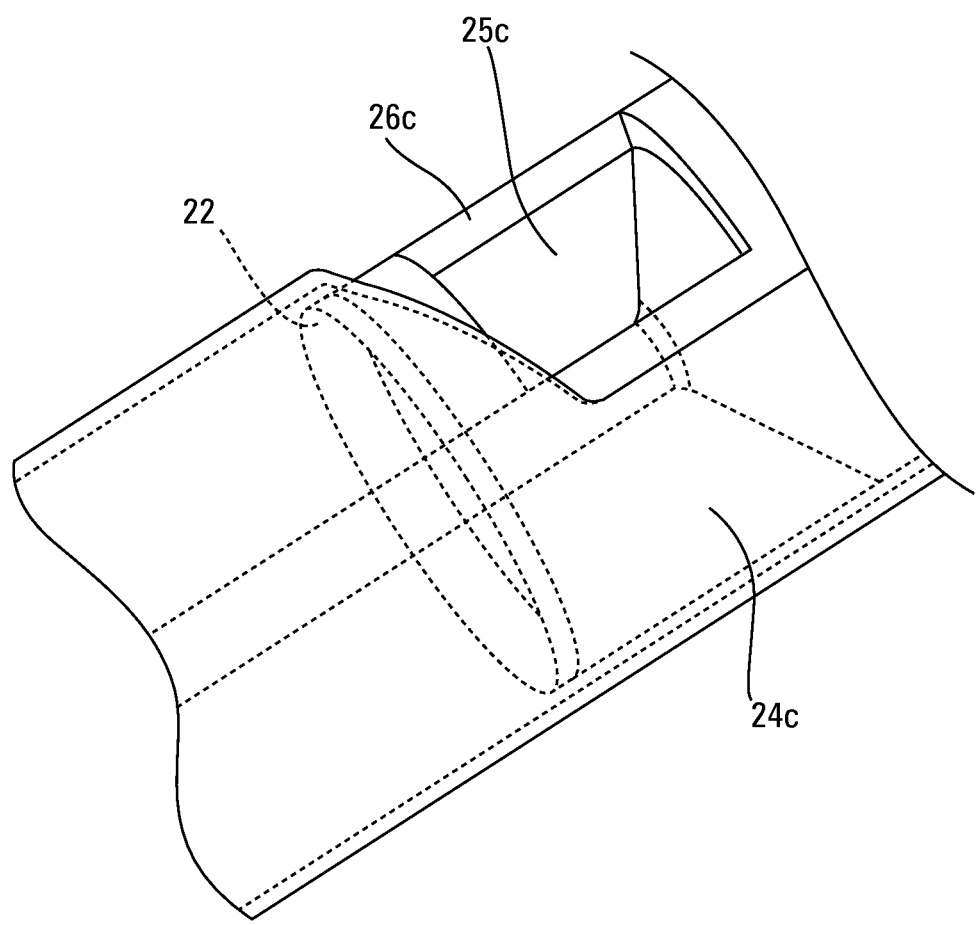
Figure 12:
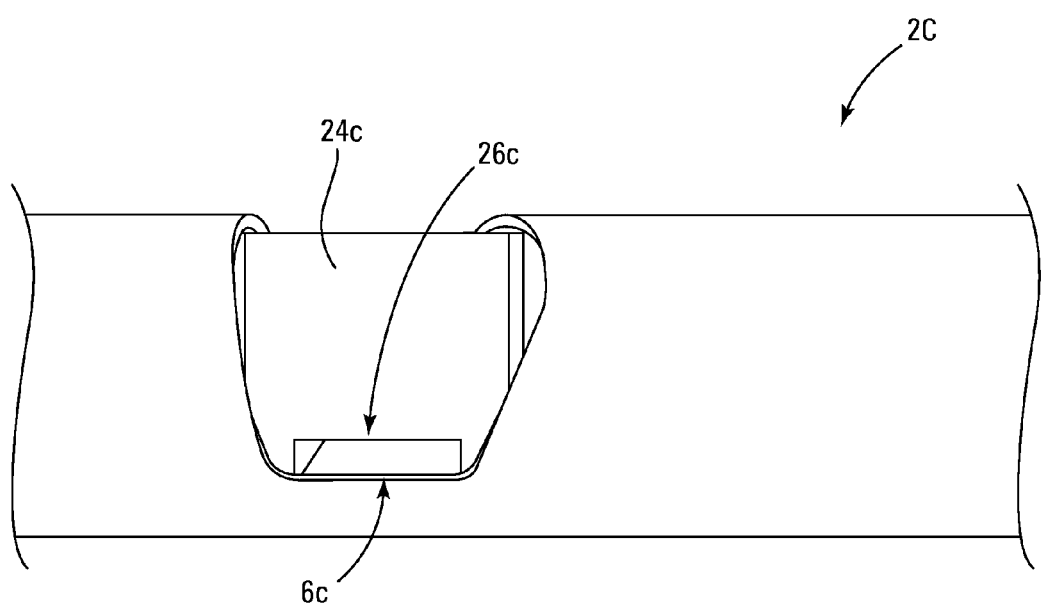

FIGS. 10 to 12 show another catheter embodiment. Catheter 2C is shown wherein the same or similar reference numbers of catheter 2C refer to the same or similar structures of catheter 2 and all discussion concerning the same or similar features of catheter 2 are equally applicable here unless noted otherwise. Compared to catheter 2, catheter 2C has an elongated cup shaped surface 24c of the cutting element 4c with a larger radial surface area than previously described corresponding cup shaped surfaces of cutting element 4. Additionally the elongated cup shaped surface 24c has an opening 25c with side cutting blade 26c which aids in material collection capability. Thus, cutting element 4c has two separate cutting structures and cutting positions. In the first cutting position as shown in FIG. 10, cutting element 4c is angularly extended through opening 6 as discussed above. In this position cutting edge 22 extends beyond and through cutting window 6. In this position the cutting is accomplished in the same manner as described with respect to catheter 2. Specifically, catheter 2C is pulled proximally through the vessel across the treatment site (lesion) to cut plaque from the lesion. Additionally, catheter 2C can be advanced distally while material is cut by cutting blade 26c, which enters through opening 25c. The material that enters opening 25c will be pushed proximally by additional material that enters opening 25c and will then get transported proximally by any of the tissue transportation methods discussed herein, including by suction and/or by auger blades if provided. In the second cutting position as shown in FIGS. 11 and 12, the cutting element 4c is positioned within the cutting window but is not tilted outwardly. In this cutting position the cutting element 4c is rotated and any material from the vessel wall which invaginates the cutting window will be cut by side cutting blade 26c. Further, cutting window 6 may be provided with a cutting edge 6c against which cutting blade 26c acts to more efficiently cut the material. In this cutting position the catheter may remain stationary within the vessel or may be moved either proximally or distally during the cutting process. Although not shown, cutting element 4c includes a cutter drive adaptor as shown in FIG. 5 if the catheter has an optional rotating tip or a modified cutter drive adaptor if the catheter has a stationary tip.

Figure 16:
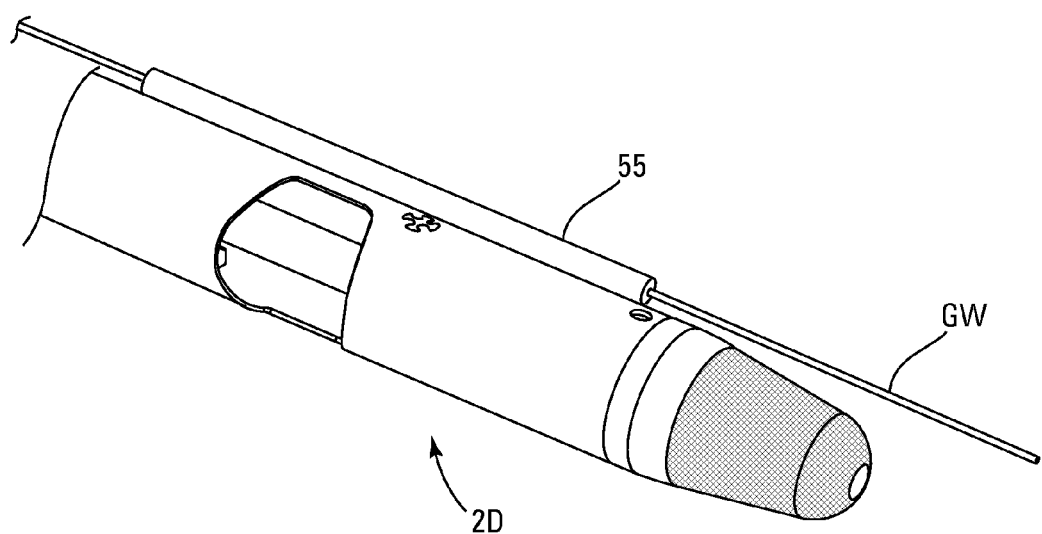
FIG. 16 is an alternative embodiment of the catheter configured for use as a rapid exchange catheter.

FIG. 16 shows an alternative embodiment of the catheter which has been constructed to be used as a rapid exchange catheter. Catheter 2D is shown wherein the same or similar reference numbers of catheter 2D refer to the same or similar structures of catheter 2 and all discussion concerning the same or similar features of catheter 2 are equally applicable here unless noted otherwise. Catheter 2D includes a side mounted tubular portion 55 which forms a relatively short guidewire lumen for receipt of a guidewire GW. Side mounted tubular portion 55 may be 1 to 30 cm long depending upon the application and is positioned not to interfere with cutting window 6. Additionally, side mounted tubular portion 55 is not attached to rotating tip 7, if the catheter is provided with a rotating tip.

Methods of using the catheters described herein are shown in FIGS. 17A, 17B, and 17C. A guidewire (GW) is percutaneously introduced into a patient's body and advanced to a region of interest in a patient's blood vessel V. If the treatment site (T) is a CTO, as shown in FIG. 17A, the guidewire may be unable to cross the lesion or occlusion material (M). FIG. 17A illustrates a totally occluded lumen in which a guidewire (GW) has been advanced to the proximal side of the occlusion material (M) of the treatment site (T). Catheter 2 has been advanced over the guidewire to a position just proximal of the occlusion material (M). During advancement the cutting element is in its stored position. In order to enable the catheter 2 to treat this occlusion it must first cross the occlusion. A traditional prior art catheter would either have to be forced across the lesion or treatment would have to be abandoned in favor of another form of treatment. With catheter 2 the occlusion material (M) may be safely crossed by energizing the drive motor to rotate the drive shaft. Rotation of the drive shaft with the cutting element in the stored position causes the abrasive tip 7 to rotate. The abrasive surface on tip 7 cuts through even calcified material enabling the catheter to be slowly advanced through the lesion or occlusion material (M) until the cutting window 6 is adjacent the distal end of the lesion as shown in FIG. 17B. The material cut by the rotating tip may be aspirated through the lumen of the catheter body as previously described. With catheter 2 in the position shown in FIG. 17B lever 13 of handle 5 is moved from the forward position to the rearward position which results in the cutting element moving proximally from the stored position to the cutting position. With the cutting element in this position pull wire 30 is pulled proximally to cause the tilt bushing 31 to move proximally with respect to ramp surface 14 of the cutter drive adaptor. This results in cutting element 4 being tilted outwardly in the manner described previously to expose the cutting edge out the cutting window. When the cutting edge is exposed the catheter 2 is pulled proximally across the lesion to cut material from the lesion as shown in FIG. 17C. The cut material is directed through the cutting window and into the collection chamber. This cutting process can be repeated by advancing and retracting the catheter across the treatment site until a sufficient amount of material has been removed. At any time during the procedure, debris may be suctioned through the catheter or fluid may be introduced to the vessel through the catheter. Additionally, at any time during the procedure the guidewire may be removed and debris may be suctioned through the guidewire lumen or fluid may be introduced to the vessel through the guidewire lumen.

Although the method of use has been described with respect to catheter 2 the procedure for use of catheters 2A, 2B, 2C and 2D is similar. For example, catheter 2A, shown is FIGS. 7 and 8, is used in a similar manner. The narrowed diameter of the drive shaft immediately proximal to the cutting element allows the cutter to tilt through the cutting window without causing the drive shaft to move laterally which might obstruct the window. Further, during use the cutting element of catheter 2A can be withdrawn proximally to pack material which has been cut and then moved distally back to the cutting position. Catheter 2B, shown in FIG. 9, is used in a similar manner with the additional feature that the auger blades pull cut material entering the cutting window proximally to reduce the possibility of the cutting window becoming obstructed with cut material during the cutting process. Catheter 2C, shown in FIGS. 10 to 12 may be used in the manner described above. Specifically, in the first cutting position catheter 2C can be moved across the treatment site in a proximal direction to cut material with cutting edge 22 and can be advanced distally across the treatment site to cut material with cutting blade 26c. Catheter 2c can be moved distally and proximally across the treatment site as many times as necessary to remove a desired amount of diseased material. Additionally, catheter 2C may be used with the cutting blade in the second cutting position as described above. In the second cutting position catheter 2C will cut material which invaginates the opening 25c while the catheter is stationary or while catheter 2c is moved distally or proximally across the treatment site. Catheter 2D, shown in FIG. 16, is used as described above except that it is advanced to the treatment site over a guidewire positioned in the guidewire lumen defined by side mounted tubular portion 55.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents. Further, while choices for materials and configurations may have been described above with respect to certain embodiments, one of ordinary skill in the art will understand that the materials and configurations described are applicable across the embodiments.

What is claimed is:

1. A catheter for removing material from a vascular lumen comprising:
    a tubular body having proximal and distal ends and a wall defining a lumen, the wall having a side opening positioned proximal of the distal end of the tubular body and an outer diameter adjacent the side opening;
    a rotatable shaft disposed within the lumen of the tubular body;
    a cutting element coupled to the rotatable shaft, the cutting element and rotatable shaft being longitudinally moveable within the tubular body between a stored position in which the cutting element is positioned distal of the side opening and a cutting position in which the cutting element is contained within the lumen of the tubular body and longitudinally aligned with the side opening;
    a cutting element exposure member within the tubular body, the cutting element exposure member being longitudinally moveable relative to the tubular body and the cutting element between a distal position and a proximal position, the cutting element exposure member being configured such that movement of the cutting element exposure member from the distal position to the proximal position when the cutting element is in the cutting position results in movement of the cutting element from the cutting position to an extended position in which a portion of the cutting element is extended through the side opening beyond said outer diameter of the wall of the tubular body.

2. The catheter of claim 1 further comprising:
    a rotatable tip connected to the distal end of the tubular body; and
    a connector assembly for selectively coupling and uncoupling the rotatable tip from the rotatable shaft.

3. The catheter of claim 2 wherein the connector assembly comprises a first portion of the cutting element shaped to mechanically interlock with a second portion of the rotatable tip.

4. The catheter of claim 2 further comprising a guidewire lumen extending through the rotatable shaft, through the cutting element and through the rotating tip such that the catheter is configured as an over the wire catheter.

5. The catheter of claim 2 wherein the rotatable tip comprises an abrasive surface.

6. The catheter of claim 1 further comprising:
a handle attached at a proximal portion of the tubular body, the handle including a power source, a motor coupled to the rotatable shaft, and first and second control members, the first control member being coupled to the rotatable shaft, the second control member being coupled to the cutting element exposure member, the first control member being configured to move the cutting element between the stored position and the cutting position, the second control member being configured to move the cutting element exposure member between the distal position and the proximal position.

7. The catheter of claim 6 wherein the cutting element exposure member comprises a pull wire having distal and proximal ends and an arc shaped bushing connected at the distal end of the pull wire, the proximal end of the pull wire being connected to the second control member.

8. The catheter of claim 1 further comprising a material collection chamber positioned within the tubular body at a location proximal of the side opening, wherein the cutting element is longitudinally moveable within the tubular body to a material compression position located proximal of the side opening, the cutting element being configured to compress material in the material collection chamber when the cutting element is in the material compression position.

9. The catheter of claim 1 wherein the cutting element further comprises a side cutting blade configured to cut material which invaginates the side opening when the cutting element is in the cutting position.

10. The catheter of claim 9 wherein the cutting element is configured such that material from the vascular lumen is cut with the cutting edge when the cutting element is in the extended position and the catheter is moved proximally within the vascular lumen and material is cut with the side cutting blade when the cutting element is in the cutting position and the catheter is moved distally or proximally within the vascular lumen.

11. The catheter of claim 1 further comprising:
a material collection chamber positioned within the tubular body at a location proximal of the side opening; and
means to direct material removed from the vascular lumen proximally into the collection chamber.

12. The catheter of claim 11 wherein the cutting element comprises a proximally oriented cup shaped surface configured to direct material removed from the vascular lumen into the collection chamber.

13. The catheter of claim 1 further comprising means for preventing the rotatable shaft from blocking the side opening when the cutting element is in the extended position.

14. The catheter of claim 1 wherein the cutting element exposure member is selectively moveable to control the amount by which the cutting element is extended through the side opening.

15. A catheter for removing material from a vascular lumen comprising:
a tubular body having proximal and distal ends and a wall defining a lumen;
a rotatable shaft disposed within the lumen of the tubular body;
a cutting element operatively coupled to the rotatable shaft so that rotation of the shaft imparts rotation to the cutting element, the cutting element and rotatable shaft together forming a rotatable assembly that is rotatable relative to the tubular body, the cutting element having a cutting edge;
a rotatable tip connected to the distal end of the tubular body, the rotatable tip being rotatable relative to the tubular body; and
a connector assembly configured for selectively coupling the rotatable assembly to the rotatable tip so that rotation of the rotatable assembly relative to the tubular body imparts rotation to the rotatable tip relative to the tubular body and selectively uncoupling the rotatable tip from the rotatable assembly.

16. The catheter of claim 15 wherein the connector assembly comprises a first portion of the rotatable assembly and a second portion of the rotatable tip, the rotatable assembly being moveable within the tubular body between a proximal uncoupled position to a distal coupled position, the first and second portions being shaped to mechanically interlock when the rotatable assembly is in the distal coupled position.

17. The catheter of claim 16 wherein the first portion is not mechanically interlocked with the second portion when the rotatable assembly is in the proximal uncoupled position.

18. The catheter of claim 15 further comprising a guidewire lumen extending through the rotatable shaft, through the cutting element and through the rotating tip such that the catheter is configured as an over the wire catheter.

19. The catheter of claim 15 wherein the rotatable tip comprises an abrasive surface.

20. The catheter of claim 15 further comprising:
a handle attached at a proximal portion of the tubular body, the handle including a power source, a motor coupled to the rotatable shaft, and a first control member, the first control member being coupled to the rotatable shaft, the first control member being configured to move the rotatable assembly between the uncoupled position and the coupled position.

21. The catheter of claim 15 further comprising a material collection chamber positioned within the tubular body at a location proximal of the side opening, wherein the cutting element is moveable within the tubular body to a material compression position located proximal of the side opening, the cutting element being configured to compress material in the material collection chamber when the cutting element is in the material compression position.

22. The catheter of claim 15 wherein the cutting element and rotatable shaft are moveable within the tubular body between a position in which the cutting element is contained within the lumen of the tubular body and an extended cutting position in which a portion of the cutting edge is extended through the side opening beyond an outer diameter of the tubular body, wherein the cutting element further comprises a side cutting blade configured to cut material which invaginates the side opening when the cutting element is in the position in which the cutting element is contained within the lumen of the tubular body.

23. The catheter of claim 22 wherein the cutting element is configured such that material from the vascular lumen is cut with the cutting edge when the cutting element is in the extended position and the catheter is moved proximally within the vascular lumen and material is cut with the side cutting blade when the cutting element is in the position in which the cutting element is contained within the lumen of the tubular body and the catheter is moved distally or proximally within the vascular lumen.

24. The catheter of claim 15 further comprising:
a material collection chamber positioned within the tubular body at a location proximal of the side opening; and
means to direct material removed from the vascular lumen proximally into the collection chamber.

25. The catheter of claim 24 wherein the cutting element comprises a proximally oriented cup shaped surface configured to direct material removed from the vascular lumen into the collection chamber.

26. The catheter of claim 15 wherein the cutting element and rotatable shaft are moveable within the tubular body between a position in which the cutting element is contained within the lumen of the tubular body and an extended cutting position in which a portion of the cutting edge is extended through the side opening beyond an outer diameter of the tubular body, the catheter further comprising means for preventing the rotatable shaft from blocking the side opening when the cutting element is in the extended cutting position.

27. The catheter of claim 15 wherein the cutting element and rotatable shaft are moveable within the tubular body between a position in which the cutting element is contained within the lumen of the tubular body and an extended cutting position in which a portion of the cutting element is extended through the side opening beyond an outer diameter of the tubular body, the catheter further comprising:
a cutting element exposure member, the cutting element exposure member being longitudinally moveable within the tubular body between a distal position and a proximal position, the cutting element exposure member being configured such that movement of the cutting element exposure member from the distal position to the proximal position when the cutting element is in the position in which the cutting element is contained within the lumen of the tubular body results in movement of the cutting element from the position within the lumen of the tubular body to the extended cutting position.

28. The catheter of claim 27 further comprising:
a handle attached at a proximal portion of the tubular body, the handle including a power source, a motor coupled to the rotatable shaft, and first and second control members, the first control member being coupled to the rotatable shaft, the second control member being coupled to the cutting element exposure member, the first control member being configured to move the rotatable assembly between the uncoupled position and the coupled position, the second control member being configured to move the cutting element exposure member between the distal position and the proximal position.

29. The catheter of claim 27 wherein the cutting element exposure member is selectively moveable to control the amount by which the cutting element is extended through the side opening.

30. A catheter for removing material from a vascular lumen comprising:
a tubular body having proximal and distal ends and a wall defining a lumen, the tubular body having a first opening at the distal end and a second opening through the wall proximal of the distal end;
a rotatable shaft disposed within the lumen of the tubular body,
a first cutting element positioned at the distal end of the tubular body and configured to cut material from the vessel through the first opening as the catheter is moved distally through the vessel, the rotatable shaft being operatively coupled to the first cutting element so that rotation of the shaft imparts rotation to the first cutting element; and
a second cutting element positioned proximally of the first cutting element and configured to remove material from the vessel through the second opening as the catheter is moved proximally through the vessel, the rotatable shaft being operatively coupled to the second cutting element so that rotation of the shaft imparts rotation to the second cutting element.

31. The catheter of claim 30 wherein the second cutting element includes a cutting edge, the second cutting element and rotatable shaft being moveable within the tubular body between a position in which the second cutting element is contained within the lumen of the tubular body and an extended cutting position in which a portion of the cutting edge is extended through the second opening beyond an outer diameter of the tubular body.

32. The catheter of claim 30 wherein the first cutting element comprises an abrasive rotatable tip.

33. The catheter of claim 32 further comprising: a connector assembly for selectively coupling and uncoupling the rotatable tip from the rotatable shaft.

34. The catheter of claim 31 wherein the second cutting element further comprises a side cutting blade configured to cut material which invaginates the second opening when the second cutting element is in the position in which the second cutting element is contained within the lumen of the tubular body.

35. The catheter of claim 30 further comprising: a material collection chamber positioned within the tubular body at a location proximal of the second opening.

36. A catheter for removing material from a vascular lumen comprising:
a tubular body having proximal and distal ends and a wall defining a lumen, the tubular body having an opening through the wall proximal of the distal end;
a rotatable shaft disposed within the lumen of the tubular body; and
a cutting element operatively coupled to the rotatable shaft, the cutting element including:
a body having proximal and distal ends and an axis extending between the proximal and distal ends, wherein the rotatable shaft is configured to impart rotation to the cutting element so that the body rotates about said axis;
an end cutting blade at one of the proximal and distal ends of the cutting element body and extending generally transverse to said axis, the end cutting blade configured to remove material from the vessel through the opening as the catheter is moved proximally through the vessel; and
a side cutting blade extending generally along said axis of the cutting element body and configured to remove material from the vascular lumen through the opening when the catheter is stationary within the vessel.

37. The catheter of claim 36 wherein the cutting element and rotatable shaft being moveable within the tubular body between a position in which the cutting element is contained within the lumen of the tubular body and an extended cutting position in which a portion of the cutting edge is extended through the opening beyond an outer diameter of the tubular body.

38. The catheter of claim 36 further comprising a first cutting element positioned at the distal end of the tubular body and configured to cut material from the vessel as the catheter is moved distally through the vessel, wherein the first cutting element comprises an abrasive rotatable tip.

39. The catheter of claim 38 further comprising:
a connector assembly for selectively coupling and uncoupling the rotatable tip from the rotatable assembly.

40. The catheter of claim 37 wherein the side cutting blade is configured to cut material which invaginates the opening when the cutting element is in the position in which the cutting element is contained within the lumen of the tubular body.

41. The catheter of claim 36 further comprising:
a material collection chamber positioned within the tubular body at a location proximal of the opening.

* * * * *